United States Patent
Cattaneo et al.

(10) Patent No.: US 8,978,533 B2
(45) Date of Patent: Mar. 17, 2015

(54) MEDICAL IMPLANT AND METHOD FOR PRODUCING MEDICAL IMPLANT

(75) Inventors: Giorgio Cattaneo, Karlsruhe (DE); Otto Baidinger, Pforzheim (DE)

(73) Assignee: Acandis GmbH & Co., KG., Pfinztal (DE)

( * ) Notice: Subject to any disclaimer, the term of this patent is extended or adjusted under 35 U.S.C. 154(b) by 926 days.

(21) Appl. No.: 13/126,386

(22) PCT Filed: Oct. 27, 2009

(86) PCT No.: PCT/EP2009/007675
§ 371 (c)(1),
(2), (4) Date: Dec. 12, 2011

(87) PCT Pub. No.: WO2010/049123
PCT Pub. Date: May 6, 2010

(65) Prior Publication Data
US 2012/0071964 A1    Mar. 22, 2012

(30) Foreign Application Priority Data

Oct. 29, 2008 (DE) .......... 10 2008 053 659
Jan. 27, 2009 (DE) .......... 10 2009 006 180

(51) Int. Cl.
*A61F 2/90* (2013.01)
*D04C 1/06* (2006.01)

(52) U.S. Cl.
CPC .... *A61F 2/90* (2013.01); *D04C 1/06* (2013.01)
USPC ........................................................ 87/11

(58) Field of Classification Search
USPC ............... 87/8, 9, 11, 13; 623/1.15, 1.2
See application file for complete search history.

(56) References Cited

U.S. PATENT DOCUMENTS

| 20,691 A | * | 6/1858 | Bazin ................................. 87/8 |
| 487,857 A | * | 12/1892 | Rood ................................ 87/13 |
| 2,112,281 A | * | 3/1938 | Ferris ............................ 403/373 |
| 2,164,278 A | * | 6/1939 | Kellems ........................ 403/373 |
| 4,112,816 A | * | 9/1978 | Muskus .......................... 87/12 |
| 4,655,771 A |   | 4/1987 | Wallsten |
| 5,061,275 A |   | 10/1991 | Wallsten et al. |
| 5,901,632 A | * | 5/1999 | Ryan .............................. 87/13 |

(Continued)

FOREIGN PATENT DOCUMENTS

| DE | 199 13 978 | 9/2000 |
| DE | 101 27 602 | 12/2002 |

(Continued)

*Primary Examiner* — Shaun R Hurley
(74) *Attorney, Agent, or Firm* — Hamre, Schumann, Mueller & Larson, P.C.

(57) ABSTRACT

The invention relates to a medical implant, particularly a stent, having a wall (11) braided out of multiple wires (10*a*, 10*b*) said wall extending along a longitudinal axis L and curving around the longitudinal axis L at least in sections, wherein in each case at least two wire ends (12) of the wires (10*a*, 10*b*, 10*c*, 10*d*) are connected to at least two first braid ends (13*a*, 13*b*) forming a first circumferential section (16*a*) of the wall (11) extending around the longitudinal axis L. The invention is characterised in that in each case at least two first braid ends (13*a*, 13*b*) are connected to one or more second braid ends (14*a*, 14*b*), wherein the second braid ends (14*a*, 14*b*) form a second circumferential section (16*b*) of the wall (11) extending around the longitudinal axis L and following the first circumferential section (16*a*) in sequence in the longitudinal direction or the second braid ends (14*a*, 14*b*) are arranged in the circumferential direction U of the wall (11).

28 Claims, 22 Drawing Sheets

(56) References Cited

U.S. PATENT DOCUMENTS

| | | | |
|---|---|---|---|
| 5,931,076 A * | 8/1999 | Ryan | 87/8 |
| 6,622,604 B1 * | 9/2003 | Chouinard et al. | 87/11 |
| 6,945,153 B2 * | 9/2005 | Knudsen et al. | 87/1 |
| 7,135,040 B2 * | 11/2006 | Wang et al. | 623/1.51 |
| 8,122,809 B2 * | 2/2012 | Simpson | 87/11 |
| 8,616,111 B2 * | 12/2013 | Simpson | 87/11 |
| 2004/0039435 A1 * | 2/2004 | Hancock et al. | 623/1.2 |
| 2006/0116752 A1 | 6/2006 | Norton et al. | |
| 2006/0271166 A1 | 11/2006 | Thill et al. | |
| 2007/0112415 A1 * | 5/2007 | Bartlett | 623/1.15 |
| 2007/0265696 A1 * | 11/2007 | Yu et al. | 623/1.15 |
| 2009/0005847 A1 * | 1/2009 | Adams | 623/1.2 |
| 2011/0060398 A1 * | 3/2011 | Tupil et al. | 623/1.15 |
| 2012/0279030 A1 * | 11/2012 | Sheldon et al. | 28/142 |

FOREIGN PATENT DOCUMENTS

| | | |
|---|---|---|
| DE | 603 11 967 | 10/2007 |
| DE | 10 2007 012 964 | 9/2008 |
| WO | WO 2008076992 A2 * | 6/2008 |

* cited by examiner

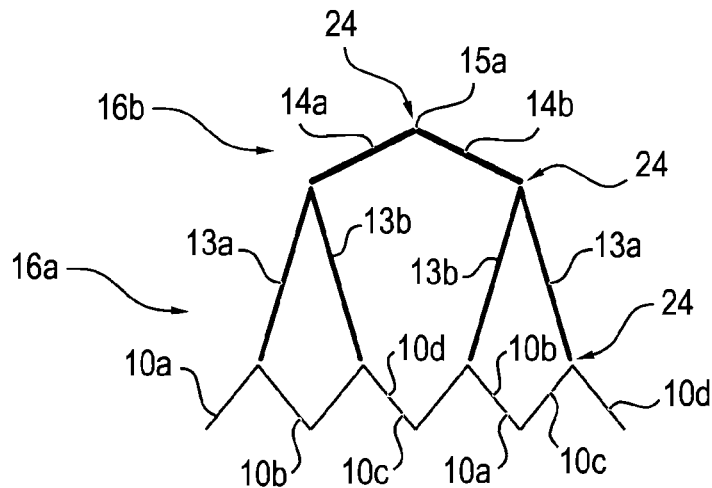
FIG. 5
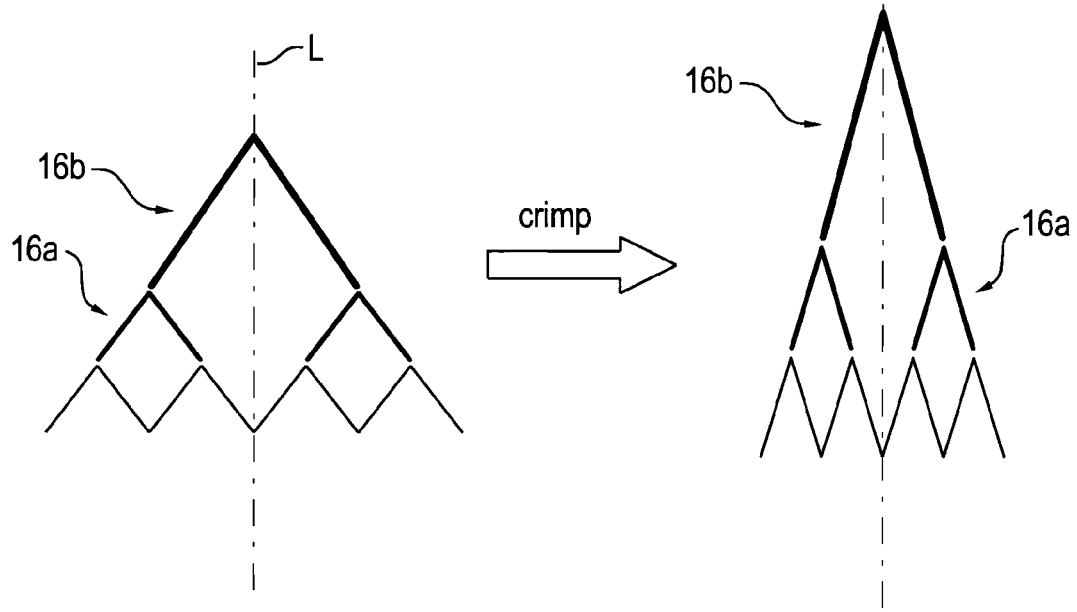
FIG. 6a
FIG. 6b

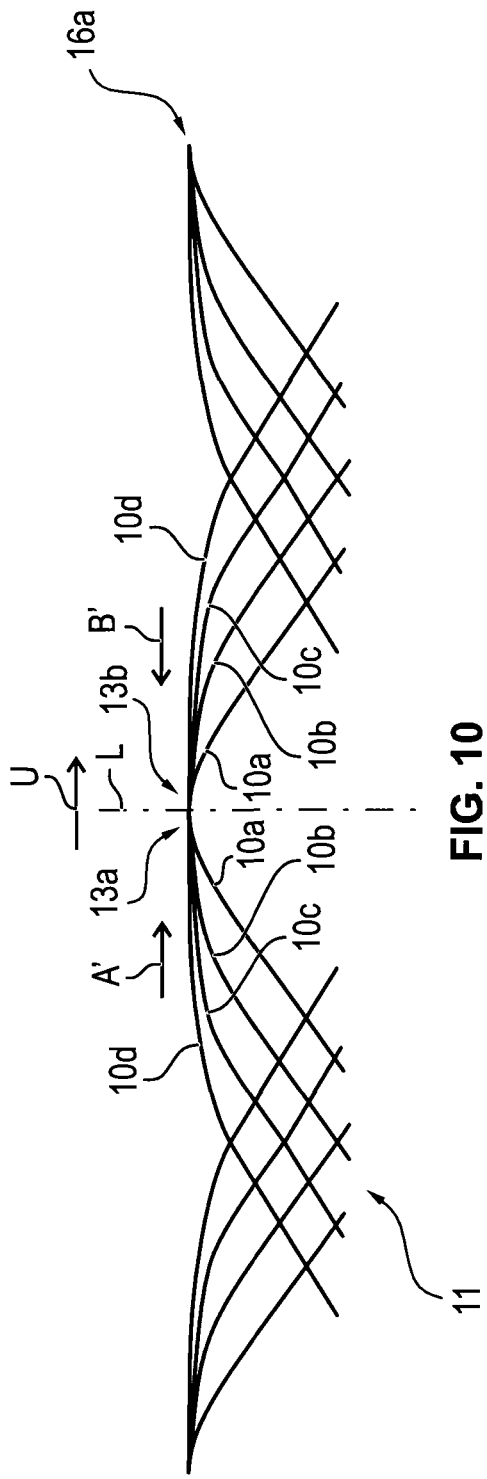
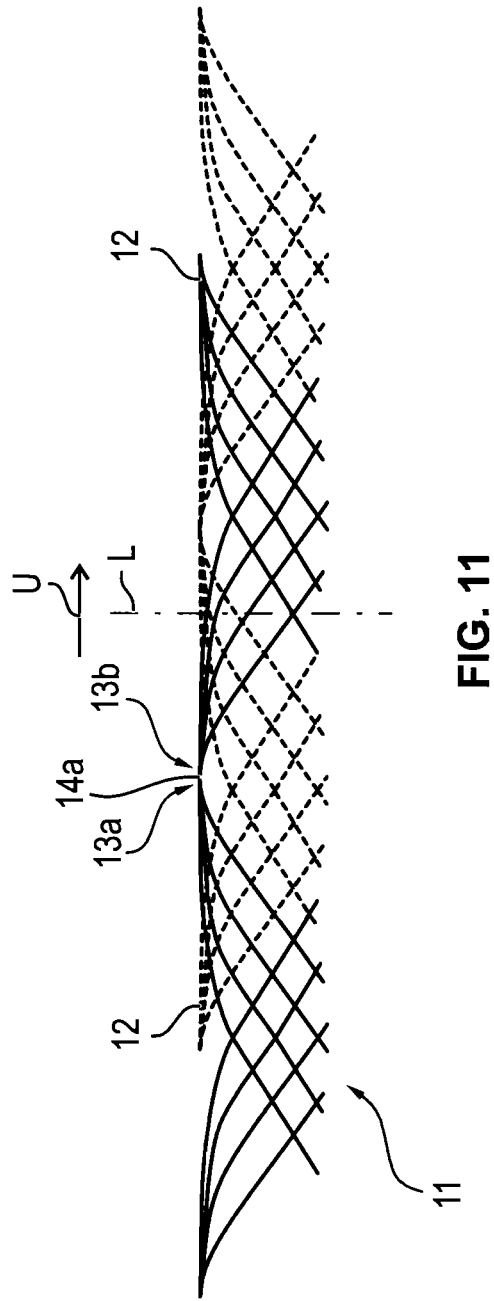

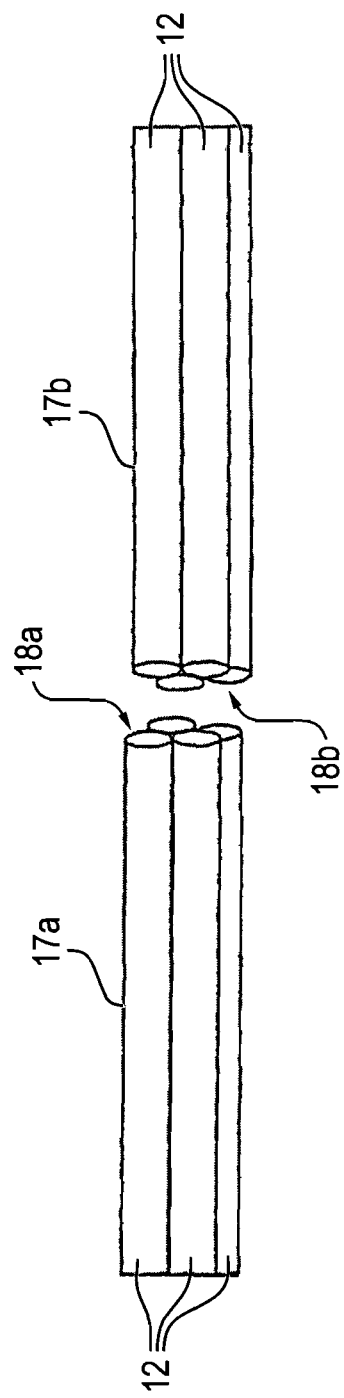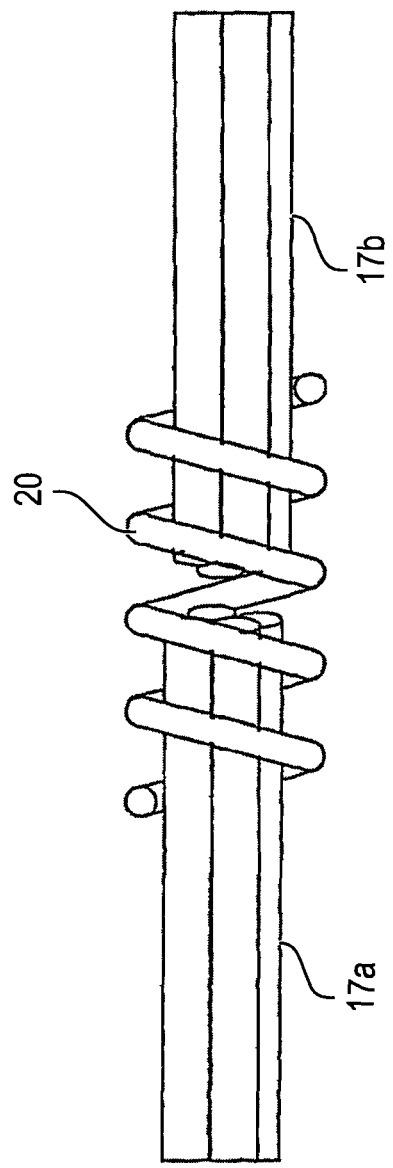
FIG. 15
FIG. 16

MEDICAL IMPLANT AND METHOD FOR PRODUCING MEDICAL IMPLANT

BACKGROUND

The invention relates to a medical implant and a method for producing an implant of this kind. An implant and a method are each known from DE 10 2007 012 964 A1.

Braided implants such as, for example, braided stents, have the advantage of being flexible and very fine-meshed. This improves the flow control during the treatment of aneurysms and the filter function during the expansion of stenoses. In addition, braided implants comprise closed cells which facilitate the repositioning of the implants since they can be drawn back into a supply system, for example a catheter.

It is known how to form stents from a single wire which changes direction many times and in doing so forms a loop at the ends in each case. The use of a single wire to produce a stent has the drawback that the entire stent has one fixed wire thickness. A further drawback of a single-wire braid consists in the fact that the fineness of the mesh of the stents is limited. In addition, the number of the wire crossovers is limited in the case of production from a single wire.

On the other hand, braided stents produced, for example, with the aid of textile machines from multiple wires have the advantage that different wall thicknesses can be formed within the same stent. The wires with a larger diameter endow the stent with strength in the radial direction. Finer wires produce a fine-mesh structure. The production of a braided stent from multiple individual wires also has the advantage that wires made of different materials can be used, wherein certain materials, such as, for example, nitinol, cobalt alloys, high-grade steel, endow the stent with the necessary strength and other materials, such as, for example, platinum and tantalum, confer X-ray visibility. The high number of wires, and hence the fine mesh structure, is particularly advantageous. It also improves automation of production.

To produce a braided stent, usually a longitudinal round braid is formed which is cut-off or cross-cut at the axial ends. This causes the formation of free wire ends at the axial edges of the stent resulting in various drawbacks:

The wires can separate and hence leave the respective crossover region in the braid. The loose wires may exert no radial force or only reduced radial force which impairs the functionality of the stents when treating aneurysms and stenoses. The free ends result in a risk of injury or risk of inflammation and the formation of stenoses, since they are able to pierce the vessel wall. Further drawbacks of braided stents with open ends occur in conjunction with a supply system, for example a catheter. For example, on crimping, the free ends can become entangled in the supply system with the consequence that the stent fails to open. This results in a risk of coagulation and impaired stent functionality. When the stent is pushed out of the supply system, eg when released by a stabiliser, a compressive force is applied to stent causing the loose wires to be heavily compressed since the structure is not stable, at least in the marginal region of the stent. Hereby, the wires can be damaged and distorted. This results in an increased risk of injury, particularly if the free wire ends are bent radially outward.

Even if no damage or compression occurs on the seating of the stents, the free wire ends can result in impaired functionality, since, due to the relatively unstable structure, the loose wires in the region of the axial stent ends do not have the necessary radial force to expand radially outward after being released from the supply system. Instead, the loose wires protrude into the bloodstream and hence increase the risk of coagulation.

U.S. Pat. No. 4,655,771 counteracts the problem of the loose wire ends in that they are connected by U-shaped connecting members, although this can induce stresses in the stent which can result in the deformation of the stent. In addition, in the case of very fine-mesh stents with a plurality of individual wires, the connection of individual wires by U-shaped connecting means is very difficult or virtually impossible from the production point of view.

U.S. Pat. No. 5,061,275 discloses a stent in which the loose ends are knobs formed by laser treatment in order in this way to counteract traumatisation. Hereby, the stability of the stent is improved by local plastic deformation of the individual wires in the region of the cross-overs or knots in the braid which is complex from the production point of view. In addition, with this stent, the radial force decreases in the region of the loose ends so that there is a risk of their protruding into the bloodstream.

DE 10 2007 012 967 A1, mentioned in the introduction, discloses an implant, for example an inliner or flow diverter embodied as a round braid and in which the individual filament ends protruding at the implant ends are brought together and connected to each other at least in pairs. The connected filament ends are atraumatically reshaped so that the risk of injury is reduced. This does not achieve sufficient improvement to the stability and atraumatic properties of the implant ends, since, on the release of the implant from a supply system, the bunched filament ends can become distorted.

BRIEF SUMMARY

The invention is based on the object of improving the implant of the type mentioned in the introduction in such a way that improved stability in the region of the implant ends is achieved and the risk of impairment to the implant functionality is reduced. The invention is also based on the object of disclosing a method for producing a medical implant of this kind.

According to the invention, this object is achieved with respect to the medical implant by the subject matter of claims.

The invention is based on the idea of disclosing a medical implant, particularly a stent, with a wall braided out of multiple wires, extending along a longitudinal axis and curving around the longitudinal axis at least in sections. At least two wire ends of the wires are each connected to at least two first braid ends forming a first circumferential section of the wall extending around the longitudinal axis. At least two first braid ends are each connected to one or more second braid ends, wherein the second braid ends form a second circumferential section of the wall extending around the longitudinal axis following the first circumferential section in sequence in the longitudinal direction. Alternatively, the second braid ends are arranged in the circumferential direction of the wall.

The invention extends beyond the implant structure known from DE 10 2007 012 964 A1; in which the individual filament ends or wire ends are connected to a first braid end which protrudes freely in the axial direction over the edge of the implant and is correspondingly sensitive (FIG. 4 of DE 10 2007 012 964 A1). In the present invention, on the other hand, a plurality ie at least two first braid ends formed from individual filament ends interact. Specifically, at least two first braid ends are connected to one or more second braid ends.

The connection of at least two first braid ends to one or to a plurality of second braid ends significantly increases the stability of the implant at the axial ends and the radial force in the region of the axial ends. This has the advantage that the wires expand radially outward which prevents elements of the implant moving inward into the bloodstream. It also prevents the first braid ends interlocking with each other. The connection of the first braid ends to second braid ends achieves increasing fixation of the braid ends. The axial ends of the implant are atraumatic.

The inventive arrangement of the second braid ends forming a second circumferential section of the wall extending around the longitudinal axis and following the first circumferential section sequence in the longitudinal direction has the advantage that the inventive principle of the interaction of a plurality of braid ends can be repeated in the longitudinal extension of the implant thus achieving a further improvement in the stability in the region of the axial implant ends.

The inventive alternative, according to which the second braid ends are arranged in the circumferential direction of the wall achieves the advantage that an implant which is substantially closed at the edges is formed with which the projection of implant elements in the axial direction is avoided, since, in the region of the implant ends or edges, these are aligned in the circumferential direction of the wall. This has the advantage that no exposed implant elements can become distorted or interlock on the release of the implant from a supply system. It is possible for the second braid ends to be arranged partially in the circumferential direction or at least predominantly in the circumferential direction. An axial component of the course of the braid end is possible. The tangential component is greater than the axial component. Braid ends arranged at least partially in the circumferential direction are more atraumatic than purely axially aligned braid ends.

The invention is further based on the idea of disclosing a medical implant, particularly a stent with a wall braided out of multiple wires extending along a longitudinal axis and curving around the longitudinal axis at least in sections, wherein at least two wire ends of the wires are connected to at least one braid end arranged in a first circumferential section of the wall extending around the longitudinal axis. The wires, whose wire ends are connected to each other to form the same braid end have the same direction of twist. The braid end is at least partially arranged in the circumferential direction of the wall. The braid end can have an axial component. The braid end can extend entirely in the circumferential direction and only have a tangential alignment.

The connection of wire ends or wires with the same direction of twist, ie only in the clockwise direction or only in the counter-clockwise direction, to one braid end ensures that the wires run smoothly into the braid end and are connected to each other without significant plastic deformation.

Since the wires or wire ends converge tangentially to each other, an abrupt angular change in the region of the connection is avoided. In the event of compression in small supply systems, there is no substantial deformation or damage to the wires. The alignment of the braid end in the circumferential direction of the wall has the advantage that the implant end lies snugly on the vessel wall when the braid is released from the introducer catheter. Hereby, the curvature of the vessel holds the implant end stable so it does not protrude radially inward into the bloodstream. The implant end extending along the vessel radius is well stabilised and hence represents a reduced risk of injury.

In a preferred embodiment of the invention, it is provided that the axial implant end, particularly the braid ends forming the axial stent end, particularly the second braid ends, comprise loop-shaped ends with a first section extending in the distal direction, a curved second section and a third section extending in the proximal direction, which distributed in the circumferential direction, connect substantially axially extending first braid ends, wherein at least two loop-shaped ends arranged immediately adjacent in the circumferential direction are connected to each other.

The interconnected and mutually supportive loops increase the overall stability of the braid since, due to the symmetry of the forces, a local equilibrium of forces prevails. The equilibrium of forces in the region of the loops means that the individual loops are fixed and, on the deformation of the implant, cannot be pressed in a circumferential direction relative to another loop. The structure of the implant is not distorted since adjacent loops are stabilised by the same force.

With this embodiment, once again, it is possible to provide more than two circumferential sections so that the inventive principle of connecting first braid ends to second braid ends can be repeated numerous times. The atraumatic loop-shaped ends forming the implant end abut the implant in the axial direction and form the termination of the braid ends which are interconnected in each case and consist of multiple wire ends in each case. Hereby, the term "first braid end" generally denotes a braid end arranged upstream in the axial direction of a further braid end, namely the second braid end. This applies to the embodiments disclosed in the application. Therefore, the invention and its embodiments are not restricted to an implant with only two braid ends arranged in sequence in the axial direction.

Preferably, the loop-shaped ends in each case comprise a group of the wire ends of the first braid end, particularly at least one, two or more than two wire ends connected to the group of the wire ends of a further first braid end. The formation of a group of wire ends, that is the use of a partial number of the wire ends of a first braid end to form the loop-shaped ends, provides the condition for differently configured implant ends with which different loops can be combined in a mutually stabilising way.

Particularly preferred is an embodiment, in which the wire ends of the first braid end in the region of the second circumferential section are branched in such a way that the groups of the wire ends form at least two loop-shaped ends arranged in opposed circumferential directions, wherein the wire ends of a branched first braid end are connected to the wire ends of a non-branched first braid end in each case. The branching of the wire ends of a first braid end achieves a screen-like structure, wherein the (during the production of the implant) free ends of the branched wire ends provide connection options for the connection to adjacent loops or wire ends. Due to its high symmetry including in the local connecting points between the adjacent groups or wire ends, this embodiment is characterised by a particularly good equilibrium of forces and hence by a particularly high overall braid stability.

The wire ends of the non-branched first braid end and the wire ends of the associated loop-shaped ends can be arranged in opposite directions, particularly abutting in opposite directions. In this way, the connecting points between the groups, loops or wire ends can be achieved with a low space requirement.

The wire ends of the interconnected groups can be arranged in parallel in the region of the connection, which achieves a particularly good fixation of the loop-shaped ends and good force transmission between the loop-shaped ends.

The wire ends of the first braid end can be connected to each other and/or to wire ends of at least one further first braid end mechanically, particularly by twisting and/or interlacing and/or by a connecting element and/or adhesively, particularly by soldering, welding or gluing. The mechanical connection achieved by twisting has the advantage that it is easy to achieve and is associated with a very low space requirement. This makes possible connections using very small connecting elements or also without connecting elements and crimping to small diameters. The mechanical connections producible by braiding have the advantage that the different interconnected sections are well stabilised. It is also possible to combine different types of mechanical connections with each other. The same applies to a combination of the aforementioned mechanical connections, namely twisting or interlacing with a connecting element. In addition, the wire ends or the groups of the wire ends can be connected adhesively to each other or one another.

In a further embodiment, the loop-shaped ends form a plurality of planes in such a way that at least one loop-shaped end overlaps a plurality of first braid ends connected to each other by loop-shaped ends. This further improves the overall stability of the implant. The loop-shaped ends can be arranged so that they overlap. This is another option for increasing the overall stability of the implant in the region of the axial ends.

In a further particularly preferred embodiment, more than two circumferential sections are provided arranged in sequence in the longitudinal direction and in each case formed by interconnected further braid ends. The repetition of the inventive principle with this embodiment according to which the braid ends formed by the joining of braid ends are again connected to form new braid ends, further increases the stability of the two implant ends.

The wires, whose wire ends are connected to form in each case a braid end and/or the braid ends, which are connected to form in each case a further braid end, can have opposing directions. This means that the interconnected wires or braid ends are arranged in different spiral directions, particularly in the case of a round braid, as with a stent. This embodiment is favourable from the production point of view.

The braid ends can in each case comprise a connecting section, wherein the connecting sections are arranged in opposite directions and connected to each other. Hereby, the connecting sections can be arranged with their end faces in a face-to-face arrangement and/or the connecting sections arranged in parallel and overlapping and/or the connecting sections connected to each other under an angle α. The arrangement of the connecting sections in opposing directions can achieve terminal connections aligned tangentially in the circumferential direction by which atraumatic implant ends are formed in a simple manner.

Alternatively, it is also possible to embody the braid ends in such a way that in each case they comprise a connecting section, wherein the connecting sections are arranged in the same direction and connected to each other. The arrangement of the connecting sections in the same direction offers the possibility of aligning the braid ends at least partially in the axial direction of the implant, ie with at least one axial component so that the braid ends aligned in such a way can be connected to other braid ends, which are also aligned with at least one axial component. This embodiment has the advantage that the connection of different braid ends can be repeated multiple times in the axial direction of the implant in a simple way.

In a further embodiment, the wires connected to wire ends to form in each case a first braid end and/or the braid ends which are connected to form in each case a further braid end, at least in the region close to the connection of the wire ends or at least in the region close to the connection of the braid ends, have the same angle of twist. This means that wires or braid ends consisting of multiple wires converge in the opposite direction under the same angle in the region of the respective cross-over point. The resulting symmetrical, at least in regions, structure of the implant facilitates the crimping of the implant, wherein distortions of the braid are substantially avoided.

It is also possible for two, three or more than three wires and/or braid ends per connection to have the same angle of twist. The wires and/or braid ends with the same angle of twist can be grouped, particularly in pairs or multiples, wherein in a group with the same angle of twist different, particularly opposed, winding directions can be combined. For each connection, it is possible for a plurality of groups, particularly two, three or more groups with different braid angles to be combined.

The wires in the region of the connection of the wire ends and the first braid ends can have different angles of twist. The wires in the region of the connection of the wire ends can, therefore, have the same angle to each other but a different angle than the bundled first braid ends following in sequence. The same applies to the braid ends provided in circumferential sections following in sequence in the axial direction which can have the same angle of twist to each other, but a different angle of twist than the braid ends following in sequence in the axial direction. With this embodiment, the wires and the first braid ends formed from these wires are arranged in the longitudinal direction with different braid angles. The same applies to braid ends which are provided in circumferential sections following in sequence in the axial direction. Generally, the angle of twist can differ in the longitudinal direction, particularly between different circumferential sections.

The different angle of twist in the longitudinal direction enables the properties of the implant to be varied in regions.

With a particularly preferred embodiment, two interconnected braid ends comprise at least one braid end which, adjacent to the connecting region, is bent between the two connected braid ends. This causes a braid end itself to be bent and the connecting point between the two braid ends to be arranged symmetrically relative to the two braid ends. The curvature of the braid end increases the restoring force or the outwardly acting radial force in the region of the implant ends.

Hereby, the wires of the curved braid end can be twisted or wound. This has the advantage that no wire is entirely located on the outer edge of the bend so that no wire is bent excessively but the bending is divided uniformly between all wires. Particularly in the case of small wires, this has the advantage that they follow the bending well thus achieving a good ratio between the bending radius and the wire cross section. This results in a high degree of flexibility and good crimpability of the implant. In addition, the restoring force is increased by the twisting or winding of several wires, which overall contributes to the overall strength.

With another embodiment, the wires, whose wire ends are connected to form in each case a first braid end, have the same direction. This means that the wires of a braid end in the region of the connection, particularly before the joining or connection to form a braid end, all run in the same direction. This embodiment is particularly suitable in combination with the inventive arrangement of the second braid end in the circumferential direction of the wall. This causes the wires to converge tangentially to each other and to be connected to the first braid end which avoids deformation or damage to the wires during compression in small supply systems.

Hereby, at least two first braid ends, each formed from wires arranged in the same direction before the connection to the braid end, can be arranged in opposing directions and connected to form the second braid end. This achieves a closed implant end which extends substantially in the circumferential direction without axially protruding components.

It is possible for 3, particularly 4, particularly 6, particularly 8, particularly 12, particularly more than 12 wires to be provided in one braid end. It is possible that 2, particularly 3, particularly 4, particularly 5, particularly 6, particularly 7, particularly 8, particularly 12, particularly 16, particularly more than 16 braid ends to be provided. The angle of twist in the region of the braid ends or directly before the braid ends can be greater than 10°, particularly greater than 20°, particularly greater than 30°, particularly greater than 40°, particularly greater than 50°, particularly greater than 60°, particularly greater than 70°.

In a further embodiment, at least two braid ends are connected to each other by a connecting element. The connecting element provides the possibility for influencing the tension between the braid ends and hence the restoring force. Advantageously, the connecting element is elastic so that it undergoes elastic deformation on the crimping of the stent. On the expansion of the stent, the restoring force of the connecting element results in an expansion of the braid ends into the original position.

Advantageously, the connecting element may be brought from an expanded state into a compressed state so that the restoring force in the region of the braid ends can be adjusted. Hereby, in expanded state, the connecting element advantageously applies a force to the braid ends connected by the connecting element in such a way that the braid ends are pressed apart. This increases the radial force of the implant on expansion. It is also possible for the connecting element only to fulfil the function of the connection and not to undergo deformation in the crimped state.

The connecting element can comprise a connecting coil, a connecting sleeve, connecting wires or other similar components.

Preferably, the connecting element comprises a middle section with connecting ends, wherein the connecting ends are connected to at least two braid ends. This design of the connecting element enables a separation of functions, wherein the middle section is designed, for example, to generate a high radial force and the connecting ends ensure a reliable connection of the middle section to the braid ends.

The middle section can comprise a U-shaped wire in use and/or a U-shaped coil in use. The U-shaped embodiment is present at least in use. This can take the form of a U-shaped preformed connecting element which, in its standby position, that is without the application of external force, is U-shaped. Alternatively, the wire or the coil, or the connecting element generally can adopt a curved shape by connection to the braid ends. In standby state, that is also without the application of external force, the respective element can be stretched, for example. Generally, in standby state the element can be wider than the spacing of the braid ends to be connected, for example if the spacing between the ends of the U-shape in unconnected state is greater than the spacing between the braid ends so that connection is to be established against the spring resistance of the element. The result is that the connecting element exerts a residual force on the braid ends when the stent is in the standby state and the reinforcement of the axial stent ends, or implant ends is achieved.

The exemplary embodiment of the connecting element as a multiple connector connecting more than two braid ends provides a further possibility for connecting the braid ends to each other in an efficient manner.

BRIEF DESCRIPTION OF DRAWINGS

The invention will now be described with respect to exemplary embodiments with reference to the attached schematic diagrams which show.

DETAILED DESCRIPTION

Figure 1:
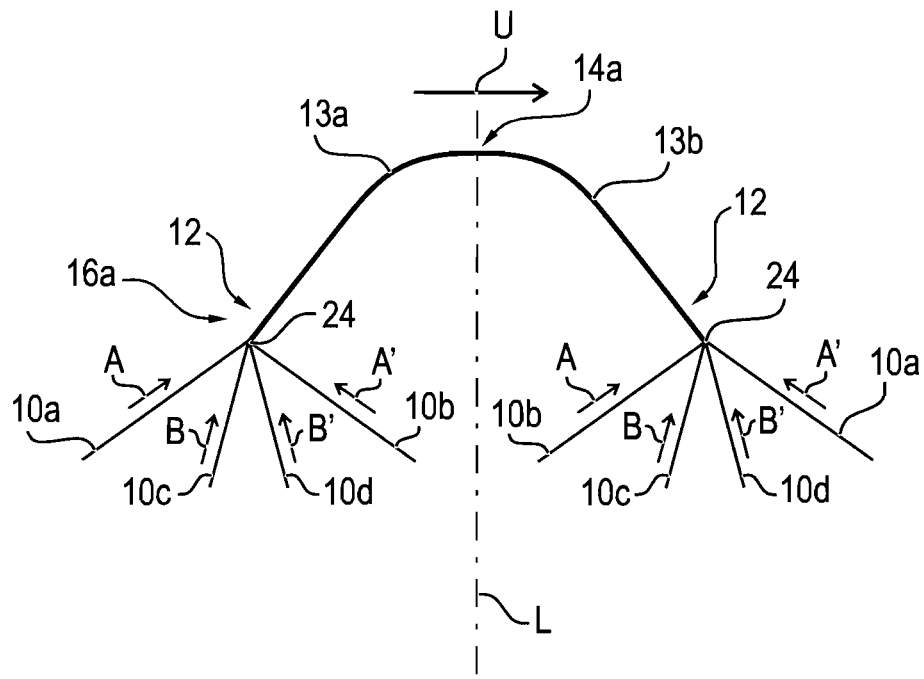
FIG. 1 a detail of the axial end of a stent according to an inventive embodiment with braid ends arranged in opposing directions FIG. 2 a detail of the axial end of a stent according to a further inventive embodiment with braid ends arranged in the same direction FIG. 3 a detail of the axial end of a stent according to a further inventive embodiment in which the wires have different angles of twist FIG. 4 a detail of the axial end of a stent according to a further inventive embodiment in which the angle of twists at the height of the connection are the same FIG. 5 a detail of the axial end of a stent according to a further inventive embodiment in which the angles of twist in the longitudinal direction are different FIGS. 6a, 6b an example of the change in the mesh structures on crimping FIG. 7 a detail of the axial end of a stent according to a further inventive embodiment in which more than two circumferential sections are provided formed by the connection of braid ends FIG. 8 the stent according to FIG. 7, wherein additionally a connecting element is arranged between the axially outwardly arranged braid ends FIG. 9 a detail of the axial end of a stent according to a further inventive embodiment in which the wires are connected tangentially to braid ends and extend in the same direction FIG. 10 the stent according to FIG. 9, wherein the connection second braid ends is depicted FIG. 11 a larger detail of the axial end of the stent according to FIG. 10
Figure 2:
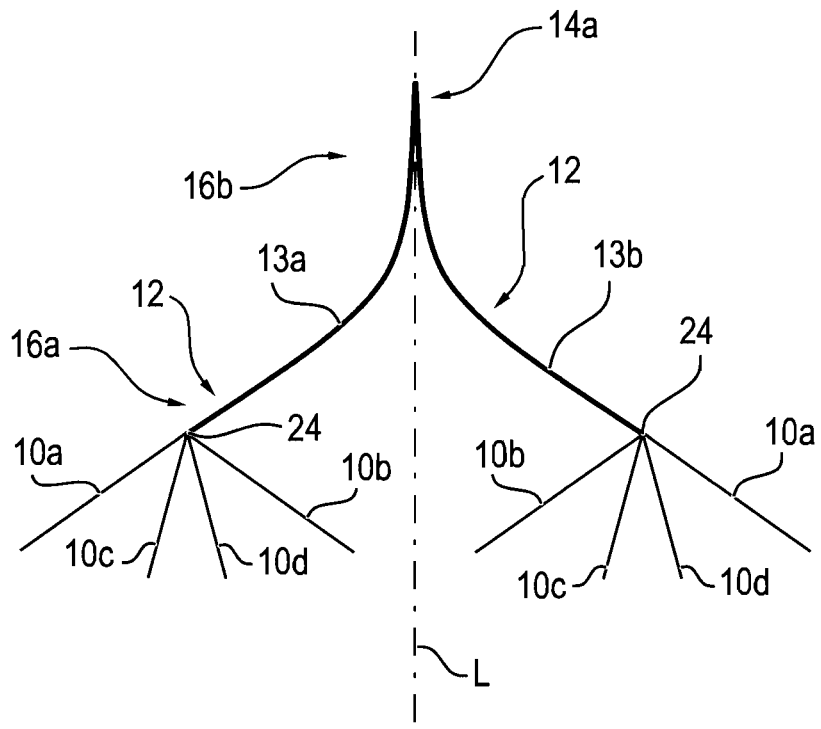

FIGS. 1 and 2 show two different examples of implant ends suitable for use, for example with stents, particularly self-expandable stents. The depictions according to FIGS. 1 and 2 and the other depictions of the exemplary embodiments in the diagrams show, for purposes of clarity, a detail of the axial end of a stent. In this case, this is a braided stent, the wall 11 of which (see FIGS. 9, 10 and 11) comprise plurality of individual wires or filaments with the same winding or spiral direction and in each case offset axially relative to each other in the longitudinal direction of the stent. These wires or filaments intersect with a corresponding number of further individual wires or filaments wound in the opposite direction, that is they have a different winding or spiral direction and are also offset to each in the axial direction of the stent. This wall, braided in a way known per se, forms a round braid, which can be implanted by means of a suitable supply system, for example an introducer catheter, in a vessel, particularly a blood vessel. To this end, the cross section of the round braid can be changed in way known per se so it is introduced into the supply system and expands in the blood vessel after release from the supply system.

The invention is not restricted to stents but generally comprises medical implants having a wall braided out of multiple wires extending along a longitudinal axis L and curving around the longitudinal axis L at least in sections. These can be, for example, flow distributors or other rotationally symmetrical implants. It is also possible that, the invention can relate to implants which are flat in standby state and are brought to curved state on implantation.

In addition, the invention is not restricted to stents or implants in which the braid is produced from individual wires. Rather, it also encompasses implants with braids braided from multiple or folded filaments or wires.

The stents according to FIGS. 1 and 2 comprise axial ends formed from the wire ends 12 of the wires 10a, 10b, 10c, 10d, wherein the wire ends 12 are arranged on the circumference of the respective axial end of the stent. The depictions in this and other attached diagrams depict in each case details of the axial ends of stents. For purposes of clarity, the associated braided wall 11 has been omitted and is only shown in regions in FIGS. 9-11. The connections of the different braid ends shown in the diagrams are distributed on the circumference of the axial ends of the stents. The invention is not restricted to the individual connections of the braid ends but comprises implants, particularly stents, in which a plurality of these connections are provided on the circumference of an axial end side by side and/or in sequence in the longitudinal direction.

With the exemplary embodiment according to FIG. 1, it is clearly evident that in each case at least two wire ends 12, with the exemplary embodiment according to FIG. 1 specifically 4 wire ends, the wires 10a, 10b, 10c, 10d are connected to at least two first braid ends 13a, 13b. In the braid of the wall 11, the wires 10a, 10b, 10c, 10d are partially braided to each, other and/or to further wires. In the distal region before the respective first braid end 13a, 13b, the wires 10a, 10b, 10c, 10d are arranged spaced apart from each other and brought together at the proximal side of the respective first braid end 13a, 13b. The wires 10a, 10b, 10c, 10d meet in the first cross-over point 24 and are connected to form the first braid end 13a, 13b. To connect the wire ends 12 to the first braid end 13a, 13b, the wire ends 12 can, for example, be twisted and/or wound or also twisted and wound in sections. They can also extend in parallel to each other or in any other configuration and can be held together by gluing, welding or soldering technology or by another element, such as, for example, a sleeve. The first braid end 13a, 13b hence comprises a bunch or a group of connected wire ends 12 formed from the wires 10a, 10b, 10c, 10d. In this diagram, this is indicated by the slightly thicker line used for the first braid ends 13a, 13b.

This applies to all exemplary embodiments of the application.

As in the case with the exemplary embodiment according to FIG. 1, it is also provided in the exemplary embodiment according to FIG. 2 that the wires 10a, 10b, 10c, 10d, whose wire ends 12 are connected to form in each case a wire end 13a, 13b, have opposing directions A, A', B, B'. Opposite directions should be understood to mean opposed spiral or winding directions of the wires. Specifically, the wires 10a, 10c arranged directly side by side have spiral directions A, B, which are directed opposite to the spiral directions A', B' of the two other wires 10b, 10d arranged directly side by side. The wires 10a, 10b, 10c, 10d are arranged in pairs, wherein in each case a wire pair has opposite directed winding directions. It is possible for there to be a plurality of wire pairs for each braid end. The exemplary embodiments according to FIGS. 3 to 8 are designed correspondingly in this regard.

The invention is not restricted to 4 wire ends 12 or 4 wires 10a, 10b, 10c, 10d for each braid end 13a, 13b, but can comprise 3, 4, 6, 8, 12 and more than 12 wires 10a, 10b, 10c, 10d for each braid end 13a, 13b, 14a, 14b, 15a, 15b. The invention is also not restricted to the connection of two braid ends, but can comprise more than two braid end pairs. In particular, the invention can comprise 2, 4, 5, 7, 8, 12 and more than 12 braid ends 13a, 13b, 14a, 14b, 15a, 15b.

This applies to all exemplary embodiments disclosed in this application.

In order to facilitate the connection of the first braid ends to at least one further braid end, at least two first braid ends 13a, 13b are required.

As may be identified from FIG. 1, the first braid ends 13a, 13b form a first circumferential section 16a of the wall 11 extending around the longitudinal axis L. The first circumferential section 16a delimits a rotationally symmetrical, particularly cylindrical envelope curve, which, in the region of the axial end of the stent, determines its lumen. A plurality of first braid ends 13a, 13b, connected to each other in each case, particularly in pairs, can be arranged on this imaginary envelope curve or on the first circumferential section 16a.

At the stent-side, the first circumferential section 16a is delimited by the cross-over point 24. Axially to the outside, the first circumferential section 16a is delimited by the outer contour of the stent and forms the outer edge of the stent.

As FIG. 1 shows, the two first braid ends 13a, 13b are arranged symmetrically to the longitudinal axis of the stent. An asymmetric arrangement is also possible. The braid ends 13a, 13b according to FIG. 1 are bent convexly toward each other and connected to each other. The connection of the two first braid ends 13a, 13b forms a second braid end indicated with reference number 14a. With the exemplary embodiment according to FIG. 1, the second braid end 14a also forms the termination of the stent in the axial direction. To this end, the second braid end 14a is arranged in the circumferential direction U of the wall 11 and comprises the connecting region of the two first braid ends 13a, 13b. In the marginal area of the axial stent end, the two first braid ends 13a, 13b extend tangentially to circumferential direction U. The braid ends 13a, 13b are arranged in opposite directions.

Contrary to the exemplary embodiment according to FIG. 1, with the exemplary embodiment according to FIG. 2, the braid ends 13a, 13b are arranged in the region of the connection in the same direction. To this end, the two first braid ends 13a, 13b are arranged concavely and form a first circumferential section 16a and a second circumferential section 16b following the first circumferential section 16a in sequence in the longitudinal direction. As with the exemplary embodiment in FIG. 1, on the stent side, the first circumferential section 16 is delimited by the cross-over point 24 at which the wires 10a, 10b, 10c, 10d converge and are connected to the first braid end 13, 13b. The second circumferential section 16b is located in the region of the connection between the two first braid ends 13a, 13b. The second circumferential section 16b is hence formed by the second braid end 14a formed by the two first braid ends 13a, 13b. The second braid end 14a is hence also arranged following the two first braid ends 13a, 13b in sequence in the longitudinal direction. With the exemplary embodiment according to FIG. 2, the junction between the first circumferential section 16a and the second downstream circumferential section 16b is continuous. The two circumferential sections 16a, 16b differ substantially in that the first circumferential section 16a is formed by braid ends 13a, 13b the extension of which comprises a longitudinal component and a circumferential component. On the other hand, the second braid end 14a, which forms the second circumferential section 16b, substantially only comprises one longitudinal component in the axial direction of the stent.

Further exemplary embodiments, in which the wires 10a, 10b, 10c, 10d form first braid ends, which are in turn connected to each other to form second braid ends 14a, 14b are shown in FIGS. 3 to 6. Common to these exemplary embodiments is the fact that in each case two wires 10a, 10c or 10d, 10b are connected in each case to a first braid end 13a, 13b. As with the exemplary embodiments according to FIGS. 1 and 2, the connection takes place in the region of a first cross-over point 24. The two first braid ends 13a, 13b are hence in each case formed from two wire ends and accordingly identified in FIGS. 3 to 6 by a thicker line than the individual wires 10a, 10b, 10c, 10d. The two first braid ends 13a, 13b, specifically in FIGS. 3 to 6b these are four first braid ends 13a, 13b, are brought together in pairs and connected to form a second braid end 14a, 14b. The joining takes place in the second cross-over point 24, which follows the first cross-over point 24 in sequence in the longitudinal direction. Specifically, two second braid ends 14a, 14b are provided. These are in turn connected in the third cross-over point 24, which follows the second cross-over point 24 in sequence in the longitudinal direction, and form the third braid end 15a. The third braid end 15a delimits the outside contours of the axial stent end.

For conceptual differentiation, the first braid ends 13a, 13b and the second braid ends 14a, 14b in each case comprise a longitudinal extension with an axial and a circumferential component. The terminating third braid end 15a forms the connection of the two second braid ends 14a, 14b and hence the edge of the stent. In this context, the third braid end 15a does not comprise a longitudinal extension like the first and second braid ends 13a, 13b, 14a, 14b but denotes the connecting point between the two braid ends 14a, 14b. This applies generally to terminating braid ends forming the axial end of the implant or stent.

Figure 3:
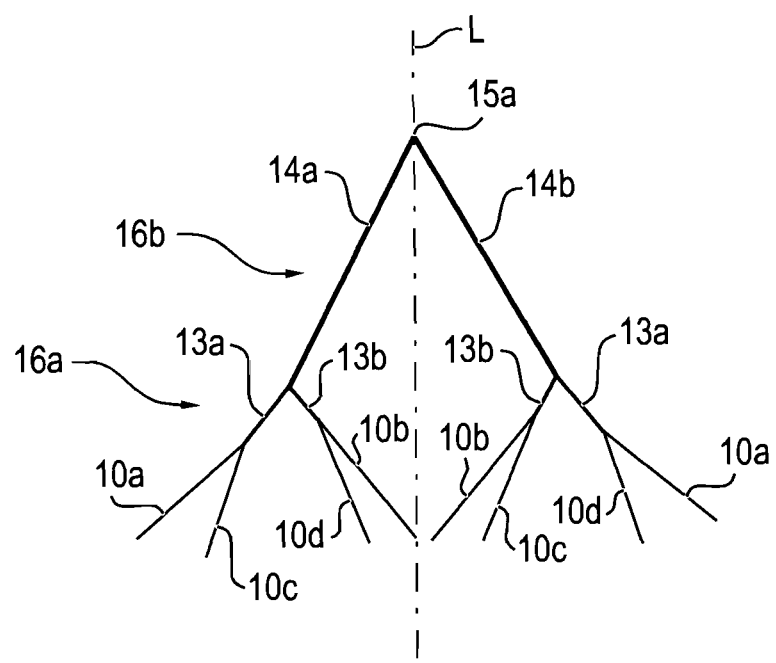
Figure 4:
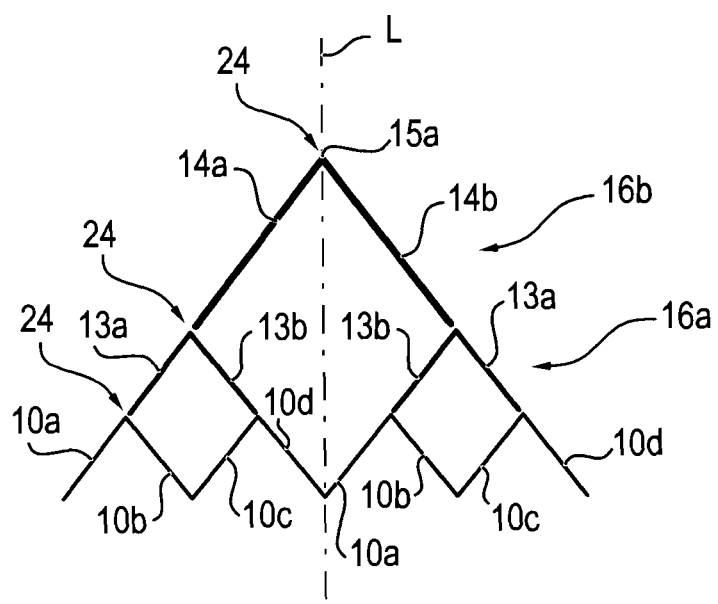

FIGS. 3, 4 show the structure of the axial stent end with two circumferential sections 16a, 16b following in sequence in the longitudinal direction, wherein the first circumferential section 16a is formed by the two first braid ends 13a, 13b and the second circumferential section 16b by the two second braid ends 14a, 14b.

With the exemplary embodiment according to FIG. 3, the wire pairs 10a, 10c and 10b, 10d forming the two first braid ends 13a, 13b comprise different angles of twist resulting in a locally asymmetrical configuration. With the exemplary embodiment according to FIG. 4, the wires 10a, 10b, 10c, 10d, whose wire ends 12 are connected to form in each case the first braid end 13a, 13b, have the same angle of twist. The same applies to the first braid ends 13a, 13b, which—just like the second braid ends 14a, 14b—in each case comprise the same angle of twist. Overall, the wires 10a, 10b, 10c, 10d and the first and second braid ends 13a, 13b, 14a, 14b are all aligned with the same angle of twist resulting in the rhomboidal structure shown in FIG. 4.

Contrary to the asymmetric structure according to FIG. 3, the symmetric structure according to FIG. 4 has the advantage that crimping to small diameters is simplified. In the case of the asymmetric braid, on crimping, the wires with a large angle of twist tend to lengthen in their spiral direction more than the wires with a flat angle. The spiral lengthens. Therefore, on crimping, there is an extension of the wires with a small angle and a compression of the wires with a large angle. Contrary to this, the wires and braid ends according to FIG. 4 are exposed to the same spiral elongation on crimping thus avoiding distortion. This is demonstrated particularly well in FIGS. 6a and 6b, wherein FIG. 6a depicts the state before crimping and FIG. 6b the state after crimping. The arrows extending in the longitudinal direction of the stent indicate the change in the length of the stent on crimping.

The exemplary embodiment according to FIG. 5 demonstrates that the elements arranged on the same circumferential section elements have the same angle of twist. The elements of different circumferential sections have different angles of twist. Therefore, the angle of twist varies in the longitudinal direction of the stent. Specifically, the wires 10a, 10b, 10c, 10d have a different angle of twist than the first braid ends 13a, 13b, which in turn have a different angle of twist than the second braid ends 14a, 14b. For example, the angle of twist of the second braid angle 14a, 14b is greater than the angle of twist of the first braid ends 13a, 13b, which in turn is smaller than the angle of twist of the wires 10a, 10b, 10c, 10d. Other variations of the braid angle are possible.

As with the exemplary embodiment according to FIG. 4, it is also advantageous with the exemplary embodiment according to FIG. 5 for the wires 10a, 10b, 10c, 10d, or generally the elements which converge in a cross-over point 24, to have the same angle of twist to each other.

Figure 7:
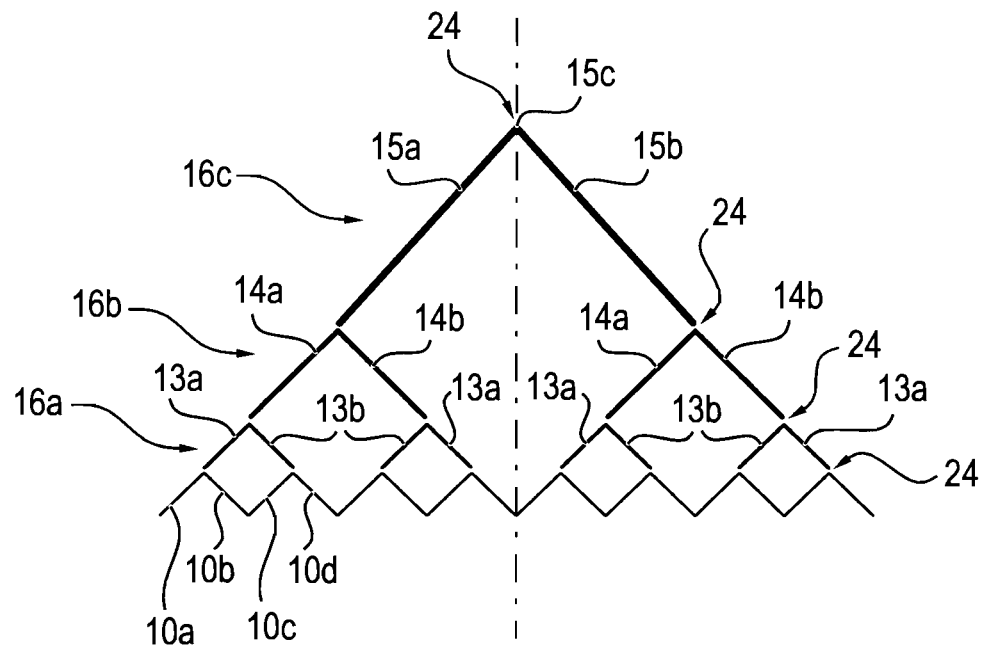

The exemplary embodiment according to FIG. 7 shows how the inventive principle of the connection of the braid ends is continued in the longitudinal direction of the stent. The stent according to FIG. 7 comprises three circumferential sections 16a, 16b, 16c, which are formed in each case by interconnected braid ends. Hereby, in each case two wires 10a, 10b, 10c, 10d are connected, particularly twisted, to a first braid end 13a, 13b. Overall, the configuration 16 depicted in FIG. 7 comprises wires 10a, 10b, 10c, 10d, which are combined or bunched to form eight first braid ends 13a, 13b. A different number is possible. The first braid ends 13a, 13b are connected in each case to second braid ends 14a, 14b which are formed, particularly braided, in each case from four wires or wire ends. Overall, the second circumferential section 16b comprises four second braid ends 14a, 14b. In each case, two second braid ends 14a, 14b are connected to a third braid end 15a, 15b to form the third circumferential section 16c. The third braid ends 15a, 15b comprise in each case eight wires and are, for example, twisted. The third braid ends 15a, 15b are connected to one fourth terminal braid end 15c delimiting the edge or the axial end of the stent.

The terminal braid end is formed from the connecting sections 17a, 17b of the upstream braid ends, which can be arranged angularly or tangentially in alignment to each other on the circumference. This applies to all terminal braid ends in this application.

Other types of connection for the braid ends are possible, wherein the braiding of the braid ends facilitates a connection with increased stability. The twisting has the advantage that the wires are brought close to each other so that the space requirement is reduced. It is also possible for both twisted and braided regions to be provided between two cross-over points 24. For example, the region of the wires adjacent to the cross-over point 24 can be braided and the region in the central area of the segment between the two cross-over points 24 can be twisted. They can also extend in parallel and be connected by other connecting methods, for example adhesively. These methods of connection are disclosed for all the exemplary embodiments described in the application.

Figure 8:
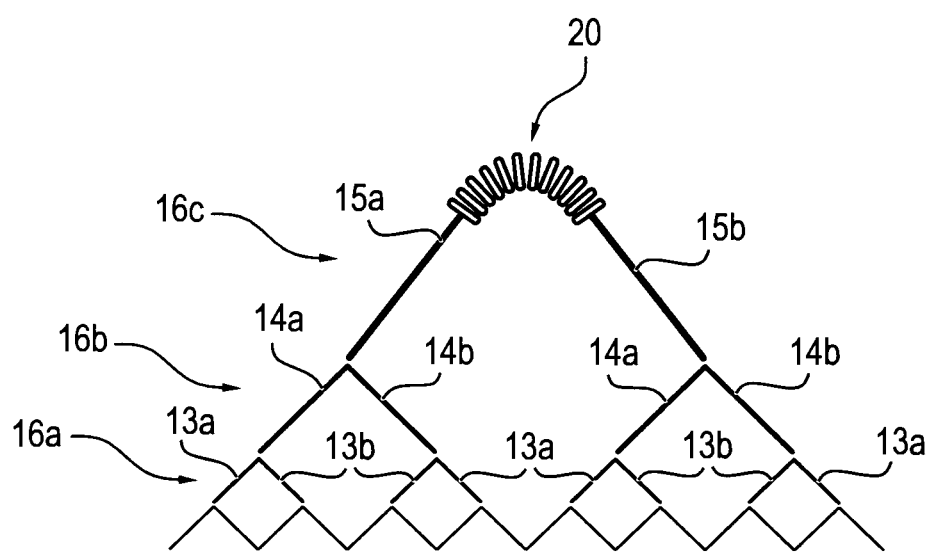

The exemplary embodiment according to FIG. 8 has the same design as the exemplary embodiment according to FIG. 7, wherein, in addition, the two third braid ends 15a, 15b are connected by a connecting element 20. As shown in FIG. 8, the connecting element 20 can be a coil. It is appropriate to twist the wires of the third braid ends 15a, 15b in the connecting region, ie in the region of the fourth braid end 15c in such a way that the fourth braid end 15c has a relatively small cross section to which the coil or another connecting element 20 can be attached.

Figure 9:
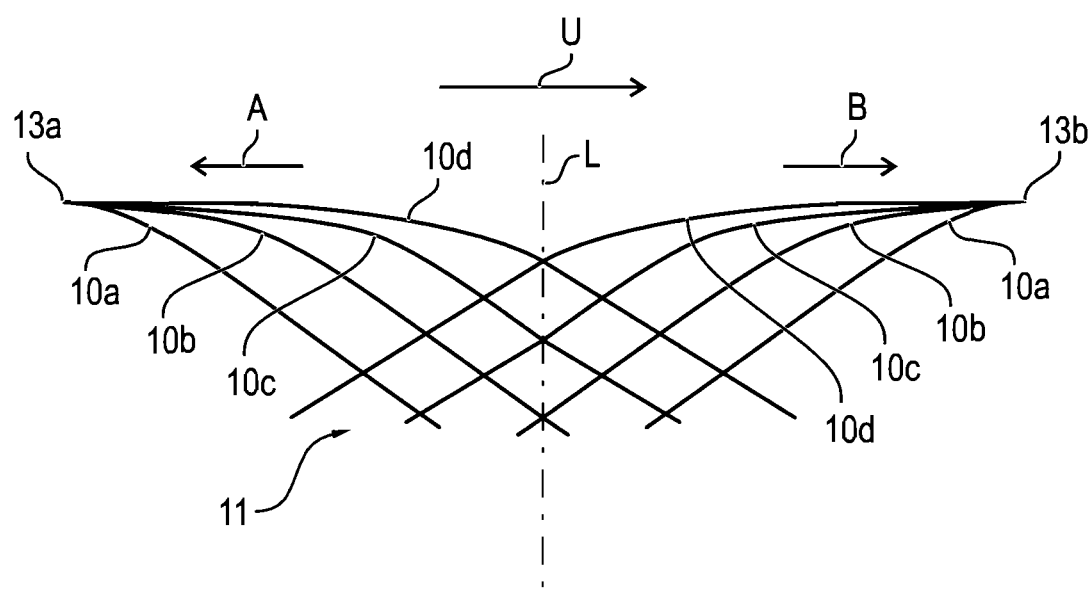

The exemplary embodiments according to FIGS. 9 to 11 demonstrate another variant in which the wires 10a, 10b, 10c, 10d are combined to form braid ends 13a, 13b or the resulting braid ends 13a, 13b are combined to form further braid ends 14a.

With the exemplary embodiment according to FIG. 9, only wires are bundled to form a first braid end 13a, 13b with the same spiral direction A, B. This has the advantage that the in each case bundled wires converge tangentially in the circumferential direction thus avoiding abrupt angle changes and deformation of the wires. The exemplary embodiment according to FIG. 9 is disclosed both independently of the principle of connecting the braid ends and in conjunction with this principle.

The connection of the first braid ends 13a, 13b by tangentially converging wires 10a, 10b, 10c, 10d is shown in FIG. 10. Here, it is evident that in each case groups of wires are connected to each other which have the same spiral direction A', B' within the group. The groups themselves have an opposed spiral direction A', B' so that the two first braid ends 13a, 13b, which are connected to each other, are arranged in opposite directions. The braid ends 13a, 13b connected in this way are at least partially or predominantly aligned in the circumferential direction U' and form the first (and only) circumferential section 16a of the axial end of the stent.

The continuation of the principle according to FIG. 10 in the circumferential direction U of the stent is shown in FIG. 11. Here it is evident that the wire ends 12 arranged in the circumferential direction U intersect with wire ends 12 coming from the opposite direction. The interconnected braid ends 13a, 13b coming from different directions are hereby connected to each other in such a way that the respective tips of the ends are aligned toward each other. This results in a loop configuration conferring increased radial force on the entire braid end. In the case of crimping, there is a reduction of the radius or angle at which the two ends are brought together. This results in the deformation of the loop causing elastic energy to be stored, which is then released when the braid is released from the supply system. This has the advantage that the vascular wall is protected. This also has the advantage of greater strength in the end region of the stent and hence better adaptation to the vascular wall.

Figure 12:
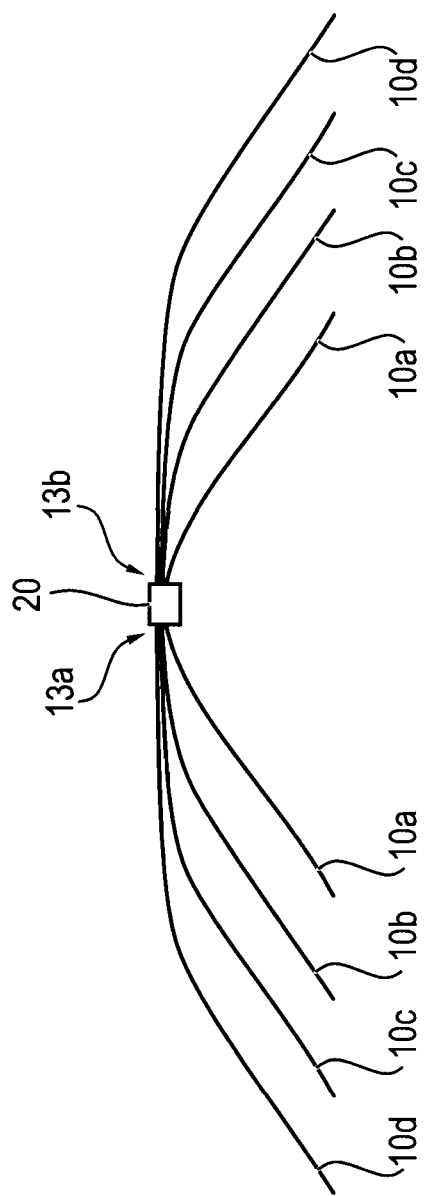
FIG. 12 a detail of the axial end of a stent according to a further example of an embodiment in which the tangentially converging wire ends are connected by a connecting element FIG. 13 the stent according to FIG. 12, wherein the wire ends are arranged in a U-shape FIG. 14a, 14b, 14c a detail of the axial end of a stent according to a further inventive embodiment in which the connecting element is a connecting coil FIG. 15 a detail of two braid ends in which the connecting sections are arranged in opposite directions FIG. 16 the connecting sections according to FIG. 15 with a connecting element FIG. 17 two connecting sections in parallel overlapping positions in the opposing direction FIG. 18 two connecting sections arranged under an angle to each other FIG. 19 two Connecting sections arranged in the same direction FIG. 20 a connecting element arranged between two braid ends FIG. 21 a detail of the axial end of a stent according to an inventive embodiment in which a plurality of connecting elements according to FIG. 20 are arranged at different levels FIG. 22 a variant of the connecting element FIG. 23 a further variant of the connecting element FIG. 24 the embodiment of the connecting element as a multiple connector FIG. 25 a connection of second braid ends of which one braid end is curved FIG. 26 a detail of the axial end of a stent according to a further inventive embodiment with mutually stabilising terminal loops FIG. 27 a detail of the stent according to FIG. 26 to elucidate the loop structure FIG. 28 a detail of the axial end of a stent according to a further inventive embodiment with a loop structure embodied in a plurality of planes FIG. 29 a detail of the axial end of a stent according to a further inventive embodiment with an overlapping loop structure FIG. 30a, 30b schematic cross-sectional views of a stent with loop-stabilised end regions FIG. 31a-d depictions of stent ends without loop-stabilised configuration and their behaviour on deformation.
Figure 13:
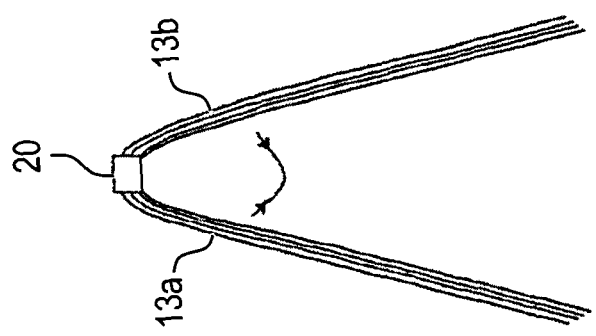

As shown in FIGS. 12 and 13, the connection between the braid ends 13a, 13b can be provided by non-positive, positive or friction locking, wherein, preferably, the connecting element 20 used is elastic and undergoes elastic deformation on the crimping of the stent. On the expansion of the stent, the restoring force of the connecting element 20 results in an expansion of the ends into the original position. The elastic element can, for example, be embodied as a coil or as a sleeve. The coil can be configured in a U-shape and be bent in a large angular range without plastic deformation. Other elastic connecting elements are also possible, such as, for example, sleeves or wires, made of plastic or metal susceptible to elastic deformation and which release the stored energy in the form of radial force on expansion. The elements can be glued, welded, soldered or connected by non-positive, positive or friction locking. For example, the connecting elements 20 can comprise plastic sleeves or metal wires. The connecting elements can be produced from material with X-ray visibility. They can also be made of spring steel or nitinol. The connecting element can be cut, lasered or etched from a material in such a way that the resulting profile can be connected to the braid ends and is possibly bendable. The connecting element can be, at least partially, a hypotube, that is a tube cut in a spiral shape. The connecting element can also comprise a cable, wherein, unlike the case with wires, no deformation occurs on crimping. The connecting element can generally be made of plastic, eg polyamide, PTFE and PE.

To generate the radial force, the connecting element can also be embodied as a moulded part which, in the standby state of the stent, exerts a force on the braid ends. This does not exclude the possibility of the connecting elements undergoing plastic deformation in addition to elastic deformation.

The aforementioned connections are disclosed for all exemplary embodiments disclosed in this application.

Figure 14A:
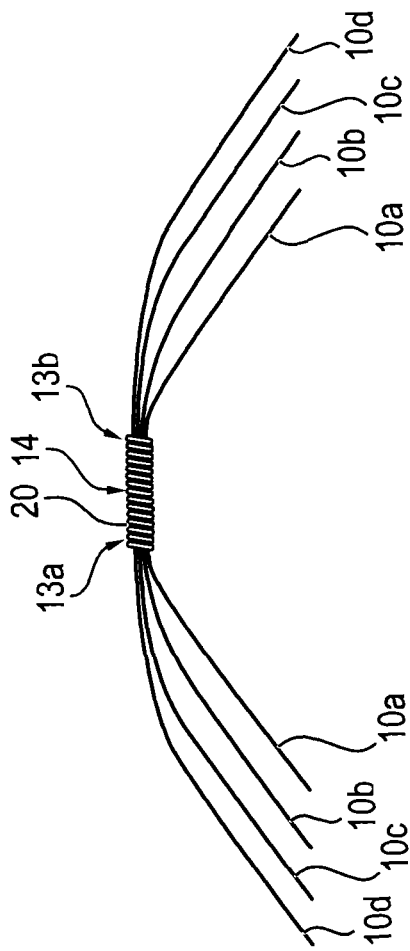
Figure 14B:
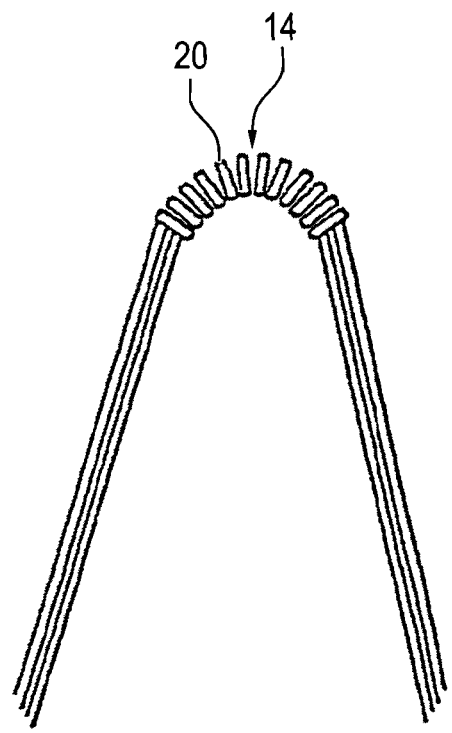
Figure 14C:
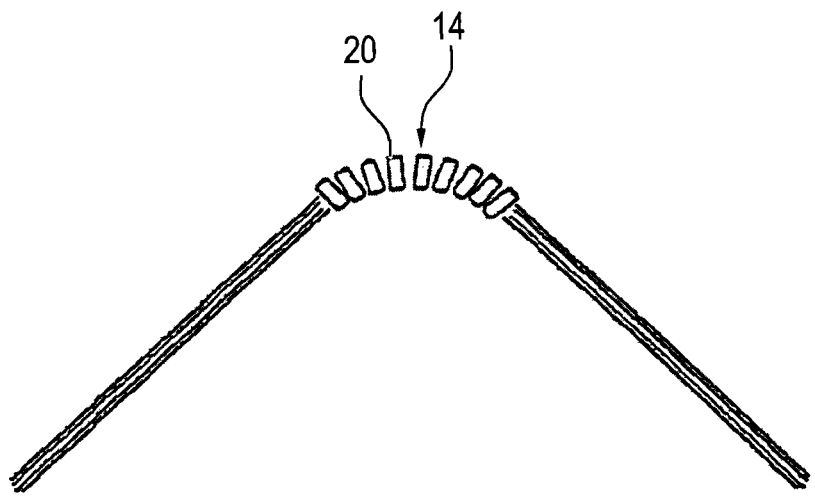
Figure 17:
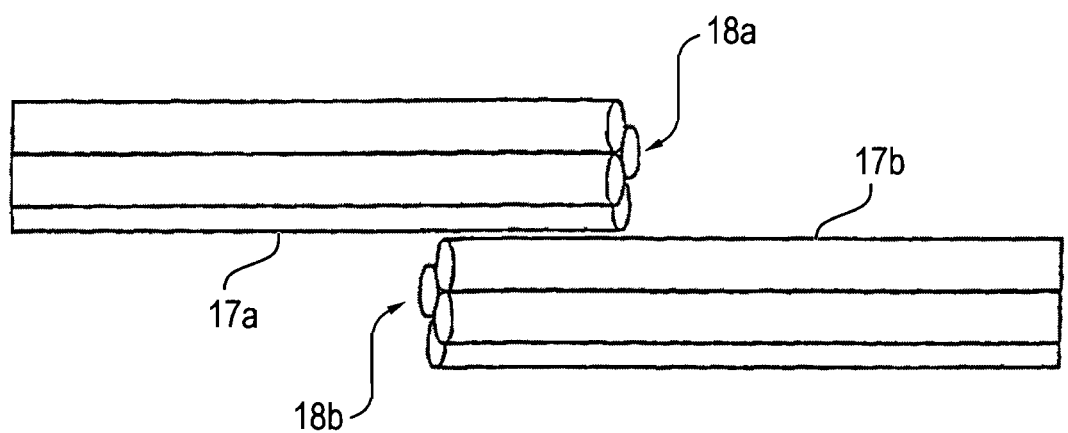
Figure 18:
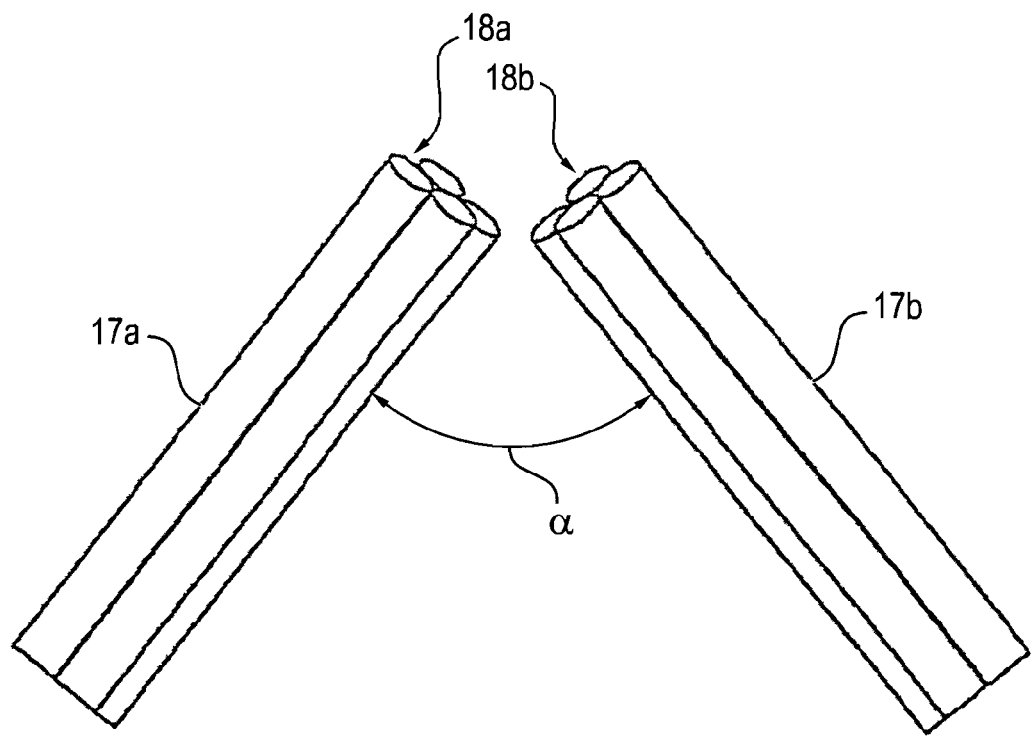

The embodiment of the connecting element as a coil is shown FIGS. 14a, 14b and 14c, wherein FIG. 14a discloses connection by a coil in the expanded state and FIG. 14b connection by a coil in compressed state. The coil can even have a U-shape in expanded state providing optimum protection for the vascular wall in expanded state (FIG. 14c).

FIGS. 15 to 19 show different examples of the embodiment of the arrangement of the interconnected braid ends, wherein the section in which the braid ends interact for connection is designated as connecting section 17a, 17b. The arrangements according to FIGS. 15 to 18 relate to the exemplary embodiments in which the braid ends 14a, 14b, 15a, 15b are arranged in opposite directions, ie the braid ends or at least the connecting sections 17a, 17b come from opposite directions, as shown, for example, in FIG. 1. With the exemplary embodiment according to FIG. 15, the connecting sections 17a, 17b are arranged with their end faces 18a, 18b in a face-to-face arrangement. The connecting sections 17a, 17b are in alignment. As FIG. 16 shows, the connection can be provided, for example, by a connecting element 20 embodied as a coil, wherein other connecting elements or types of connection, such as, for example, adhesive connections are possible. With the exemplary embodiment according to FIG. 17, the connecting sections 17a, 17b are arranged in parallel and overlapping. With the exemplary embodiment according to FIG. 18, the connecting sections 17a, 17b are connected to each other under an angle α.

Figure 19:
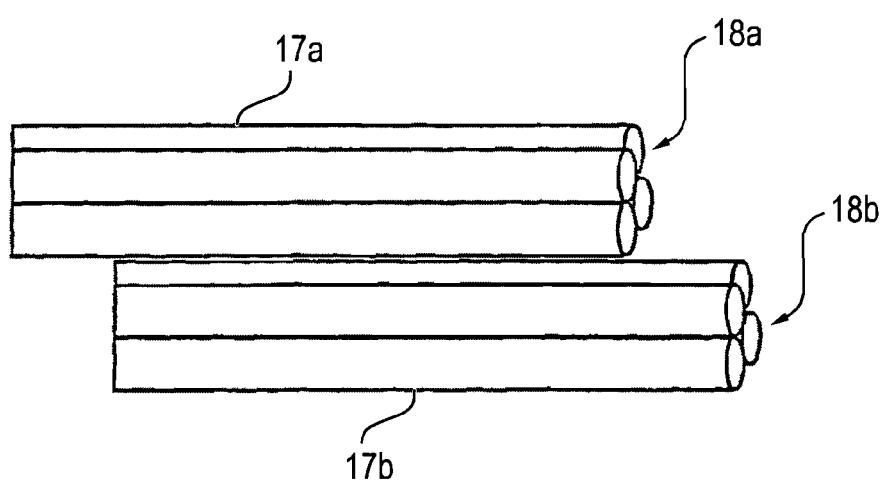

The exemplary embodiment according to FIG. 19 is particularly suitable in conjunction with the exemplary embodiment according to FIG. 2 without being restricted thereto, wherein the connecting sections 17a, 17b are arranged in the same direction and connected to each other. This means that the connecting sections 17a, 17b come from the same direction. The exemplary embodiment according to FIG. 19 is also disclosed in combination with the exemplary embodiments according to FIGS. 9 to 14. The connecting sections 17a, 17b, or the braid ends can hence be arranged tangentially in the circumferential direction.

FIGS. 21 to 25 describe different connection options. These do not show the possibilities for connecting the braid ends 13a, 13b, 14a, 14b, 15a, 15b with non-positive locking, positive locking or adhesively which are disclosed in connection with all exemplary embodiments. For example, the braid ends 13a, 13b, 14a, 14b, 15a, 15b can be welded, glued or connected in some other way.

Figure 20:
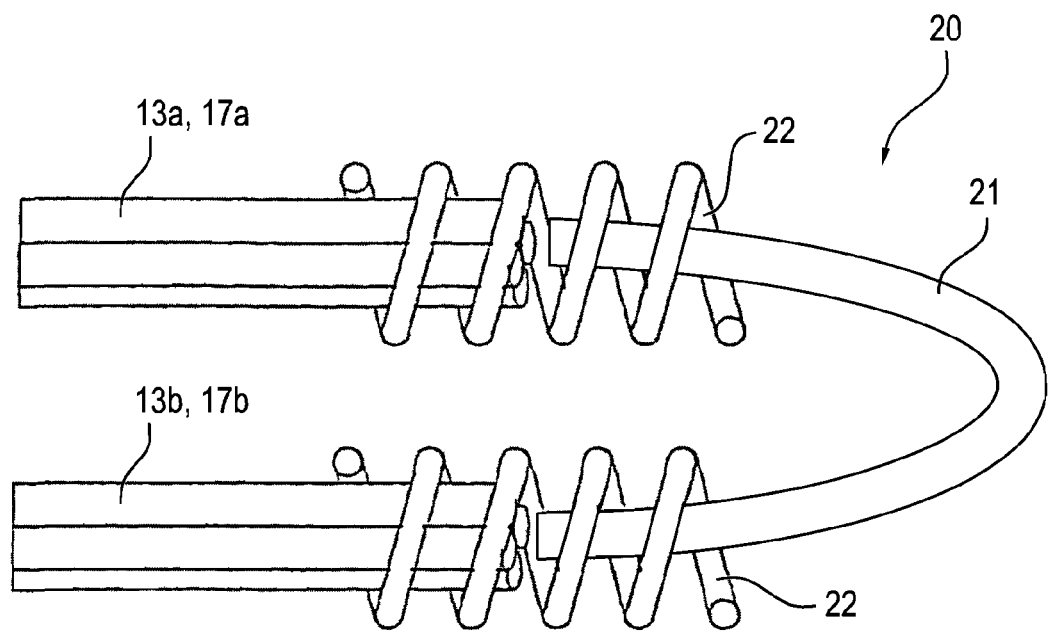

With the exemplary embodiment according to FIG. 20, the connecting sections 17a, 17b, that is the end regions of the braid ends 13a, 13b, 14a, 14b, 15a, 15b, which are connected to each other, are arranged in the same direction. These regions, or sections point, or are arranged, in the same direction. The remaining region of the braid ends 13a, 13b, 14a, 14b, 15a, 15b can be arranged in the opposing direction. FIG. 2 shows an example of this. The exemplary embodiment according to FIG. 20 is also suitable for the exemplary embodiments according to FIGS. 3 to 8 and to be precise for the connection of the external or terminating braid ends in the longitudinal direction.

The connecting element 20 shown in FIG. 20 comprises a middle section 21 with connecting ends 22, wherein the connecting ends 22 are connected to at least two braid ends 13a, 13b, 14a, 14b, 15a, 15b or to the associated connecting sections 17a, 17b. The connecting element according to FIG. 20 can be combined with all the exemplary embodiments in this application. This also applies to the other connecting elements according to FIGS. 21 to 25. With the exemplary embodiment according to FIG. 20, the middle section 21 is embodied as a U-shaped wire, wherein the connecting ends 22 comprise coils which, in connected state, reach round and hold both the middle section 21, ie the wire, and the connecting sections 17a, 17b of the braid ends 13a, 13b. For reasons of clarity, the two coils according to FIG. 20 are shown with a constant diameter. In held state, the coils are firmly connected to the wire. Instead of the coils, the wire ends of the middle section 21 can also be connected by welding, gluing or otherwise by adhesion or positive or friction locking to the connecting sections 17a, 17b. Instead of the coils, it is also possible to use sleeves or other connecting means which are glued or connected to the wire and the connecting sections 17a, 17b. The middle section 21 can comprise a plurality of wires which are twisted together. For reasons of simplicity, the wires of the braid end are shown as parallel. Preferably, the wires are connected to each other, in particular twisted or braided. This applies to all exemplary embodiments in this application.

Figure 21:
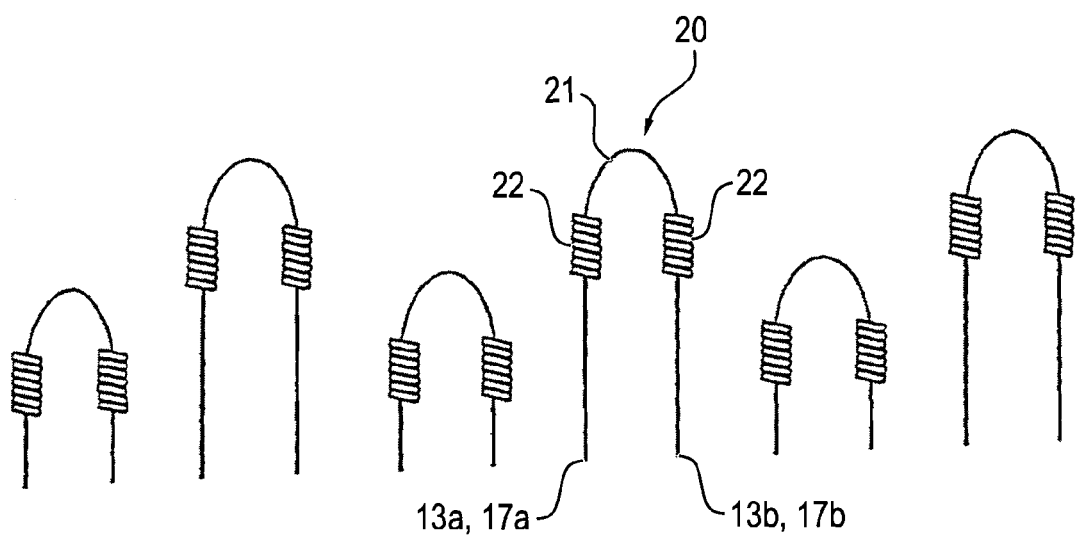

With the exemplary embodiment according to FIG. 21, the arrangement of the connecting elements 20 according to FIG. 20 is shown with reference to a stent with 12 ends, eg each made of four wires,. This arrangement is applicable to all other connecting elements. The wire elements are connected by means of U-shaped elastic connecting elements 20, wherein the connecting elements 20 are distributed offset over the circumference. This ensures that, on crimping in the supply system, the entire space requirement on the circumference is low.

Figure 22:
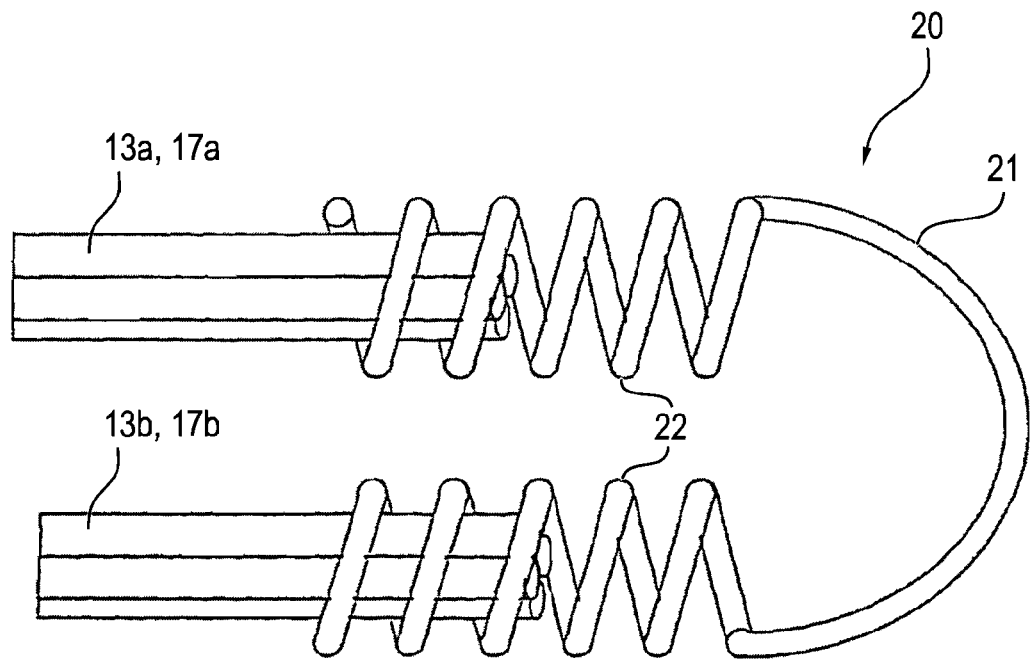
Figure 23:
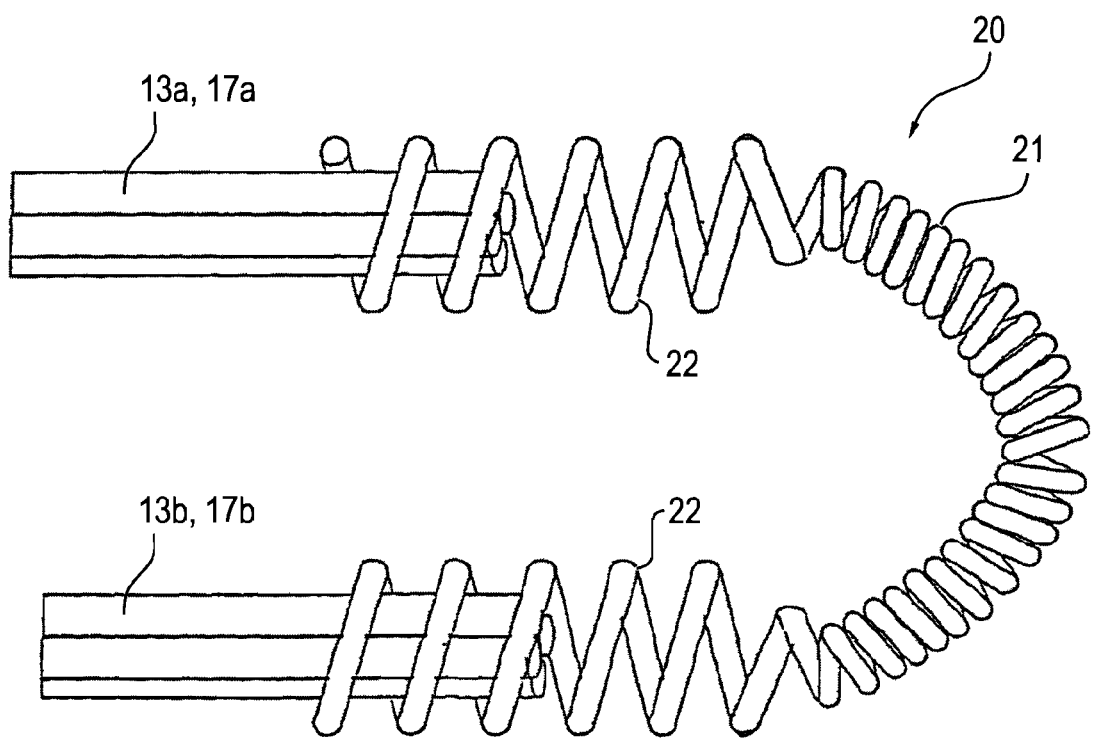

With the exemplary embodiment according to FIG. 22, the elastic connecting element comprises a wire-shaped middle section 21, which can be bent forward. The middle spacing 21 is connected in one piece to the connecting organs 22, particularly the coils. Instead of the coils, it is possible for other connecting organs or connecting ends 22, for example sleeves or an adhesive connection, to be provided. With the exemplary embodiment according to FIG. 23, the middle section 21 is embodied in a coil shape. The coil-shaped middle section 21 can be connected to coils which form the connecting ends 22 and have a larger diameter than the coil of the middle section 21. The smaller diameter of the middle coil means the connecting element 20 is easier to crimp. On crimping, the bending radius of the coil is reduced. The smaller the elastic connecting element 20, the better the element follows the bending. Hereby, the ratio between the bending radius and the cross section of the elastic element is as large as possible.

Figure 24:
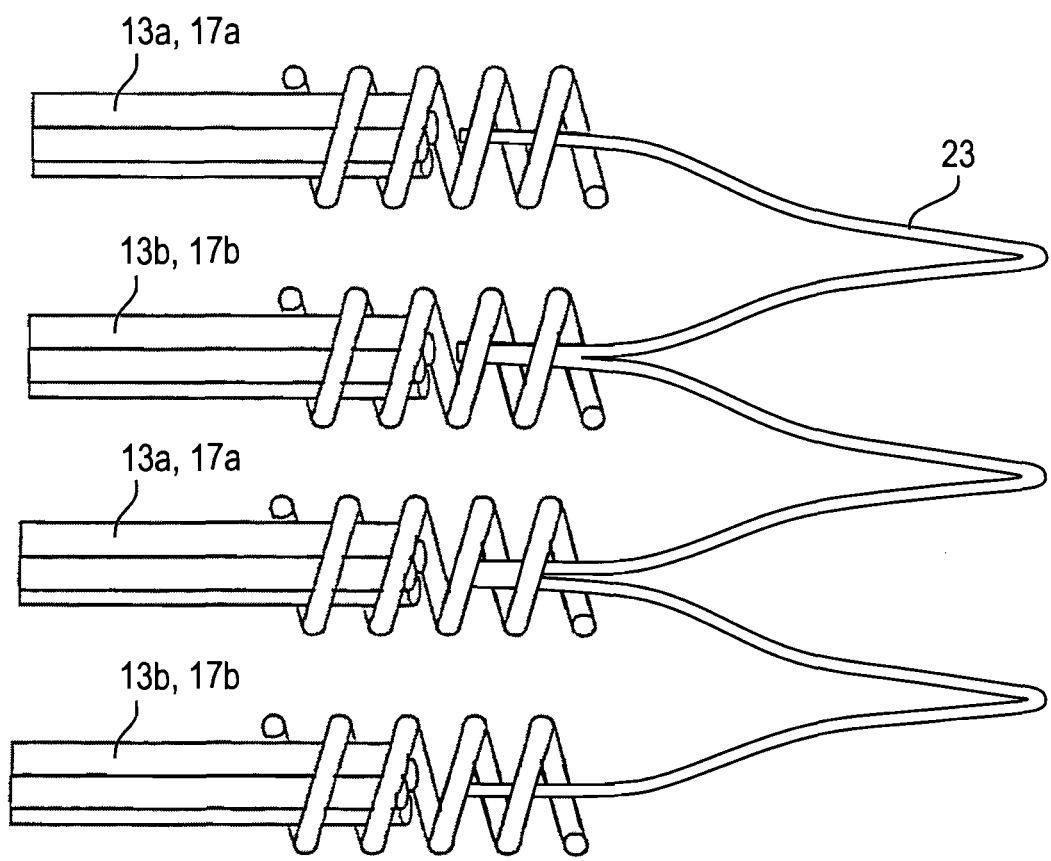

As FIG. 24 shows, the elastic connecting element can comprise a multiple connector connecting a plurality of braid ends 13a, 13b or connecting sections 17a, 17b. For example, the multiple connector can be embodied similarly to the segment of a cut-off stent.

Figure 25:
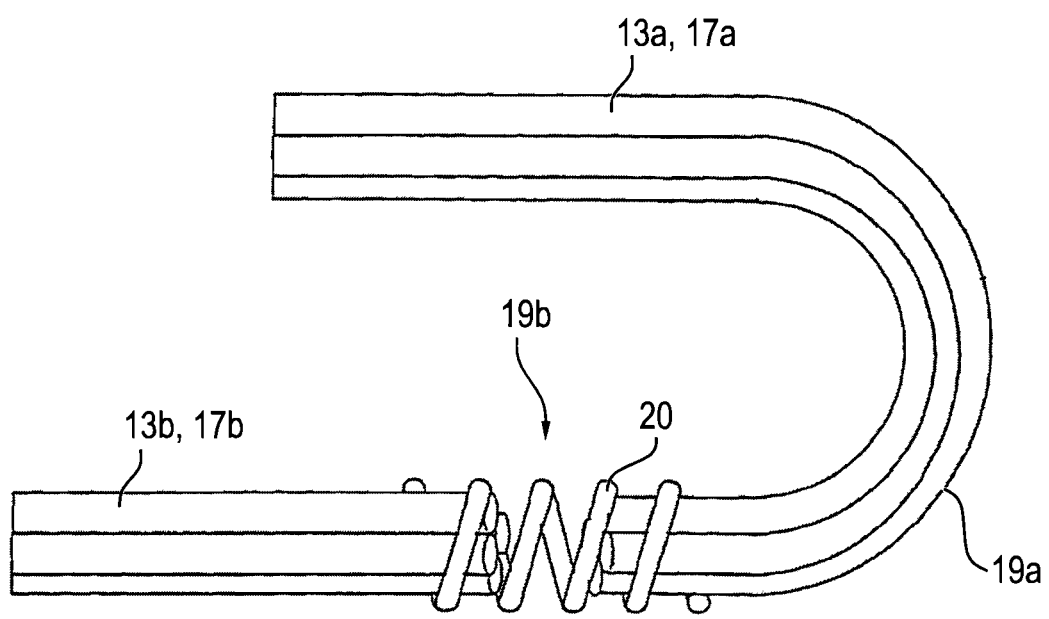

A particularly preferred exemplary embodiment for the connection of the braid ends 13a, 13b, 14a, 14b, 15a, 15b or the connecting sections 17a, 17b is shown in FIG. 25. The exemplary embodiment according to FIG. 25 is based on a similar principle as the connecting elements 20 shown in the exemplary embodiments, wherein the restoring force is also achieved by a U-shaped element bridging the spacing between the two braid ends 13a, 13b or the connecting sections 17a, 17b. Unlike, the preceding exemplary embodiments, however, a separate component is not used for this, but one of the two braid ends 13a, 13b, which is curved for this purpose. Hereby, the curved region 19a of the one braid end 13a abuts the connecting region 19b between the two connected braid ends 13a, 13b. The connection is achieved by an elastic, or even a non-elastic connecting element 20, for example by a coil or other connecting elements, such as a sleeve, wherein the elastic connecting element is preferred, since this can also bend. Here, once again, adhesive, non-positive and friction connections are possible. The connecting region 19b is located off-centre relative to the two braid ends 13a, 13b, that is not in the middle of the U-shape or the curved region 19a. A symmetric arrangement, with which the two braid ends 13a, 13b are curved is conceivable. It is also conceivable for the two braid ends 13a, 13b to overlap in the U-shape and for both to be bent, which increases the strength. They can then also be connected by a connecting technique such as gluing, welding and the like without a connecting element being required.

The exemplary embodiment according to FIG. 25 has the advantage that the braid end actually enters the bending which achieves a high restoring force by simple means. The effect can be improved if the connecting sections 17a comprise twisted or braided wires. In particular, twisting the wires has the advantage that no wire is completely located on the outer edge of the bending causing it to be excessively deformed. The exemplary embodiment according to FIG. 25 achieves a particularly good interaction between force and flexibility, as with a cable.

The exemplary embodiment according to FIG. 25 is applicable to all braid connections.

The braid, or the wall 11 itself, can be made of nitinol, or of chromium-cobalt alloys, of Elgiloy metal, or of plastic wires.

The wires are preferably equal to or smaller than 100 µm, 80 µm, 50 µm or 40 µm. It is possible that, for better connection, in one or more circumferential sections one braid end is split into 2 or more braid ends, which then run into the next braid end or even into different braid ends.

Further exemplary embodiments for inventive implants, in which a self-stabilising loop configuration is used in the region of the axial stent ends, are shown in FIGS. 26 to 30. The embodiment of the stent axial ends in loop technology is for example shown in the exemplary embodiments in FIGS. 1 to 8, insofar as the loop ends terminating the axial stent end, particularly the second braid ends are extended by the self-stabilising loop technology. The terms "first and second braid ends" generally indicate braid ends following each other in sequence in the longitudinal direction of the stent, which interact with each other, without hereby being restricted to exemplary embodiments which only comprise two braid ends following each other in sequence in the longitudinal direction, that is only two interacting planes.

Figure 26:
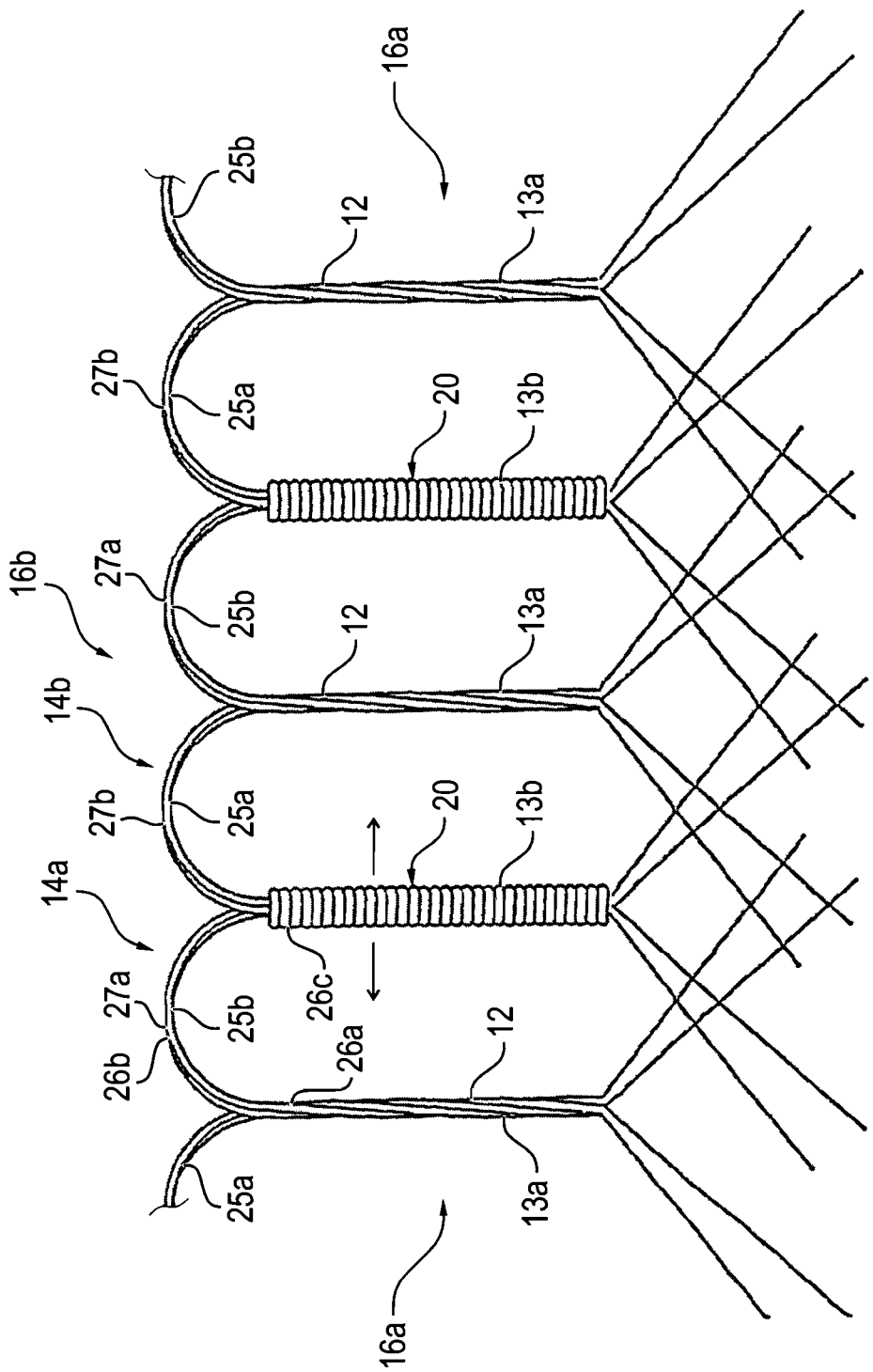

With the exemplary embodiment according to FIG. 26, this means that the invention is not restricted to the depicted interaction of the first braid ends 13a, 13b forming the first circumferential section 16a, with the second braid ends 14a, 14b forming the second circumferential section 16b or with the braid ends forming the axial implant end. Instead, it is also possible for the first braid ends 16a shown in FIG. 26 to be preceded by further braid ends in the longitudinal direction, such as, for example, shown in FIGS. 4 to 6.

For reasons of simplicity, in the following, the braid ends forming the axial implant end will be referred to as second braid ends (in the sense of braid ends following the first braid ends in sequence in the longitudinal direction).

FIG. 26 shows that the second braid ends 14a, 14b are embodied as loop-shaped ends 25a, 25b which comprise a first section 26a extending in the distal direction, a curved second section 26b and a third section 26c extending in the proximal direction. The curved second section 26b is arranged between the two first and third sections 26a, 26c extending in the proximal and distal directions and connects them. On the basis of this basic structure of the loop or the loop-shaped ends 25a, 25b, the geometry of the loop is optional. As FIG. 26 shows, it is particularly advantageous for the first and third sections 26a, 26c to be arranged in the axial longitudinal direction of the stent, hence achieving a parallel arrangement of the loop-shaped ends 25a, 25b and, associated therewith, a simple and fixed attachment of the respective loop-shaped ends 25a, 25b to adjacent loop-shaped ends 25a, 25b. The loop-shaped ends 25a, 25b connect substantially axially extending first braid ends 13a, 13b distributed on the circumference of the stent. Hereby, it is possible, as shown in FIG. 26, for the loop-shaped ends 25a, 25b to connect directly adjacent first braid ends 13a, 13b to each other. Other configurations, with which first braid ends arranged further away are connected to each other are explained elsewhere with reference to FIGS. 28, 29.

The overall stability of the braid is increased in that at least two loop-shaped ends 25a, 25b arranged immediately adjacent in the circumferential direction are connected to each other. With the stent according to FIG. 26, all loop-shaped ends 25a, 25b arranged immediately adjacent in the circumferential direction are connected to each other. It is also conceivable to connect a different number of loop-shaped ends 25a, 25b to each other, wherein the best result for the overall stability of the braid is achieved if all loop-shaped ends arranged immediately adjacent are connected to each other.

The connection of the individual loop-shaped ends 25a, 25b to each other is achieved in that the loop ends, specifically the first and third sections 26a, 26c, are fixed. With the exemplary embodiment according to FIG. 26, for example, this is achieved in that the distally extending first sections of two loop-shaped ends 25a, 25b arranged immediately adjacent in the circumferential direction are formed coming from the same first braid end 13a. Since the first braid end 13a achieves the fixation of the wire ends 12 contained therein, for example by twisting or interlacing the wire ends 12, the two first distal sections 26a continued from the same first braid end 13a, and particularly branched, are also fixed. Hence, the loop-shaped ends 25a, 25b arranged adjacent in the circumferential direction are connected to each other in this region in such a way that on the deformation of the implant or the stent there is virtually no relative movement between the adjacent loops 25a, 25b.

Figure 27:
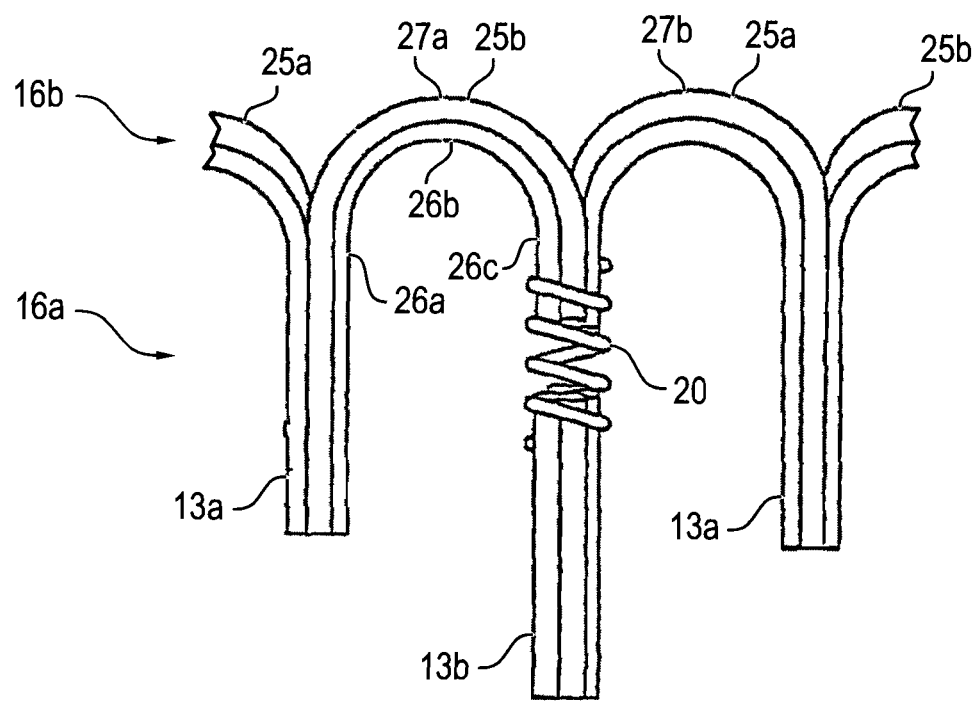

The same principle applies with the other loop end of the loop-shaped end 25a or 25b. There, the third sections 26c extending in the proximal direction of two loop-shaped ends 25a, 25b arranged immediately adjacent in the circumferential direction are brought together and combined. As explained elsewhere with reference to FIG. 27, the two proximal third sections 26c brought together are connected to each other. This can take place mechanically by twisting, interlacing and/or by fixing by means of a connecting element 20 and/or adhesively. The connection of the two proximal third sections 26c fixes the associated loop-shaped ends 25a, 25b and virtually prevents any relative movement between the two loop-shaped ends 25a, 25b. In addition, the interconnected proximal third sections 26c are connected to a third wire bundle, namely to a further first braid end 13b arranged in alignment with the two proximal third sections 26c (FIG. 27).

Other types of connection for adjacent loop-shaped ends 25a, 25b are possible. For example, the loop-shaped ends 25a, 25b can be produced as separate loops, which are in each case connected to first braid ends 13a, 13b by connecting elements 20 in accordance with the middle connection shown in FIG. 27.

In addition, it can be identified from FIG. 26 that only a part of the wire ends 12, which in each case form a first braid end 13a, 13b, that is a braid end extending in the axial direction, are used to form the loop-shaped ends 25a, 25b. Hence, the loop-shaped ends 25a, 25b in each case comprise a group 27a, 27b of the wire ends 12 of the first braid end 13a, 13b. A group 27a, 27b can, for example, consist of one, of more than one, two, more than two, three, more than three, four or more than our wire ends 12. The group 27a of the wire ends 12 of the first braid end 13a is connected to a group 27b of the wire ends 12 of a further first braid end 13b, wherein the group 27b of the further first braid end 13b is formed in a similar way as the group 27a of the first braid end 13a.

With the exemplary embodiment according to FIG. 26, the formation of the groups 27a, 27b takes place in that the wire ends 12 of the first braid 13a are branched in the region of the second circumferential section 16b. This means that the first braid end 13a is divided, wherein a part of the wire ends 12 forms a group 27a and another part the wire ends 12 forms the further group 27b. As can further be identified in FIG. 26, the two groups 27a, 27b of the wire ends 12 form at least two loop-shaped ends 25a, 25b arranged in opposed circumferential directions. The loop configuration produced in such a way has a screen-like shape. The wire ends 12 coming from a common first braid end 13a are continuously connected to the wire ends 12 of the branched groups 27a, 27b or the wire ends 12 of the common first braid end 13a form a continuation of the wire ends of the two associated groups 27a, 27b.

The wire ends 12 of the branched first braid end 13a are in each case connected to the wire ends 12 of a non-branched further first braid end 13b, wherein the unbranched first braid end 13b terminates in the region of the first circumferential section 16a, that is in the proximal side of the axial stent end, and to be precise without forming branched-off wire groups, which are continued in the distal direction.

As shown in FIG. 26, the wire string guided in a first circumferential direction or the group 27a is returned in the proximal direction with the formation of the loop-shaped end 25b in the proximal direction and connected to the next first braid end 13b in the first circumferential direction. This first braid end 13 forms a non-branched first braid end 13b, as described elsewhere with reference to FIG. 27. The other wire string coming from the common first braid end 13a or the other group 27b is returned with the formation of the loop-shaped end 25a in the proximal direction and arranged in a second circumferential direction, which is opposed to the first circumferential direction. The group 27b is connected to the next first braid end 13b in the second circumferential direction, which, as explained elsewhere with reference to FIG. 27, forms a non-branched braid end. This results in a screen-like loop configuration.

The branched groups 27a, 27b coming from the common first braid end 13a are therefore in each case connected to first braid ends 13b arranged adjacent in different circumferential directions. This means that the loop configuration is made up of alternatively arranged branched first braid ends 13a and non-branched first braid ends 13b distributed over the circumference of the stent.

In the example according to FIG. 26, the branching first braid ends 13a are in each case made up of four wire ends 12 or four wires. The branched wire ends or the groups 27a, 27b consist in each case of two wire ends connected to two further wire ends 12 of an adjacent branching further first braid end 13a. Therefore, in the region of the connection of the groups 27a, 27b, which come from different common first braid ends 13a, four wires connected to each other are present in each case.

The invention is not restricted to the number of wires shown in FIG. 26, but also comprises wire strings or groups with a different number of wires. For example, 2, 4, 6, 8, 10, 12, 14, 16 wires can be provided for each branching first braid end 13a.

The connection of the branching first braid ends 13a to the non-branched first braid ends 13b is shown in FIG. 27. Here, the division of the wire ends 12 in two groups 26a, 27b is clearly evident, wherein in each case two groups of different branching first braid ends 13a are brought together and connected to each other. The groups 27a, 27b brought together are connected to a non-branched first braid end 13b. To this end, the groups 27a, 27b forming the loop-shaped ends 25a, 25b are brought back in the proximal direction in such a way that the ends of the groups 27a, 27b are aligned with the associated non-branched first braid end 13b.

As shown in FIG. 27, the branching is embodied in the region of the first distal section 26a of the loop-shaped end 25a, 25b. The first distal section 26a passes into the curved second section which in turn passes into the third section 26c extending in the proximal direction. The third section 26c forms the region in which two adjacently arranged loop-shaped ends 25a, 25b are connected to each other. Hereby, the wire ends 12 of the non-branched first braid end 13b and the wire ends 12 of the associated loop-shaped ends 25a, 25b are arranged in opposite directions. Specifically, the end faces of the interconnected braid ends are arranged in relation to each other in such a way that the braid ends, ie the branched and non-branched braid ends 13a, 13b, are arranged in alignment or abutting in opposite directions. In the region of the proximal third section 26c, the wire ends 12 of the interconnected groups 27a, 27b are arranged in parallel.

The arrangement of the wire ends 12 within a group 27a, 27b or in the region of the first braid end 13a, 13b is explained as follows.

As FIG. 27 shows, the wire ends 12 can be arranged in parallel in the region of the loop-shaped ends 25a, 25b. It is also possible to connect the wire ends in these regions by twisting, braiding or in some other way, for example adhesively. A combination of the aforementioned types of connection is possible insofar as the wire ends 12 are arranged for example braided or twisted in the first distal section and in the second curved section and in parallel in the third proximal section. It is also possible for the wires 12 of the groups 27a, 27b coming from the different first braid ends 13a to be twisted, braided or connected adhesively to each other.

In addition, a connecting element 20, for example in the form a coil or a sleeve, is provided for the connection of the groups 27a, 27b coming from the different first braid ends 13a to the non-branched braid end 13b arranged in the opposite direction. Other embodiments of the connecting element 20 are possible.

The aforementioned braiding has the advantage that the different sections can be well stabilised. On the other hand, twisting is simple to achieve and is combined with a very small place requirement. This enables connections by small connecting elements 20 and crimping in small diameter. As mentioned above, it is possible for the branching first braid end 13a to be braided and the loop-shaped ends 25a, 25b to be twisted. This causes the branching point between the branching first braid end 13a and the loop-shaped ends 25a, 25b to be well stabilised. It is also possible for the region of the non-branched first braid end 13b within the connecting element 20 to be twisted, for example within the sleeve so that a small internal diameter of the connecting element 20 can be selected. The region outside the sleeve or the connecting element 20 is braided so that the braid end is stable. Further configurations or combinations of the different types of wire connection are possible.

The coil or the sleeve embodied for example as a connecting element 20 can be glued, welded and soldered to the wire ends 12. The face-end connection of the loop-shaped ends 25a, 25b to the non-branched first braid end saves space so that a small connecting element 20, particularly the coil or the sleeve can be selected.

The sleeve can be connected mechanically to the first braid end or the loop-shaped ends 25a, 25b, particularly by cold forming (crimping). Hereby, the sleeve is impressed in the clearances of the wire ends 12 or forms a relief cut so that a positive locking is formed between the sleeve and the wire ends 12. This type of connection is possible both in the region of the first braid end 13a, 13b and in the region of the third section 26c of the loop-shaped ends 25a, 25b extending in the proximal direction.

Figure 28:
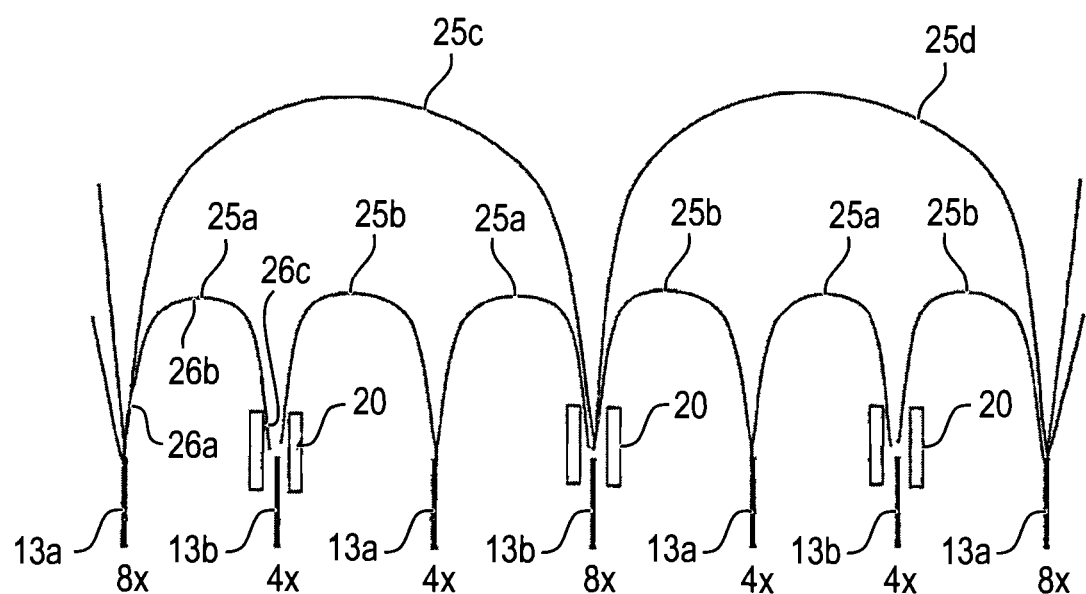

A further exemplary embodiment for the self-stabilising loop configuration is shown in FIG. 28. The above-described types of connection of the different braid ends or the wire ends 12 to each other can be used with the exemplary embodiment according to FIG. 28. The same applies to the exemplary embodiment according to FIG. 29.

The basic structure of the loop configuration according to FIG. 26, with which a first braid end 13a is connected to non-branched first braid ends 13b with the formation of two loop-shaped ends 25a, 25b extending in opposed circumferential directions is also achieved with the exemplary embodiment according to FIG. 28.

The self-stabilising effect of the loop configuration is achieved in that the loop-shaped ends 25a, 25b is formed on the one hand by dividing or branching of a wire string or first braid end so that the loop-shaped ends 25a, 25b, particularly their first distal section, are connected by the branching or that the braid end arranged upstream of the branching in the longitudinal direction. On the other hand, the ends, ie the third sections of the loop-shaped ends 25a, 25b returned in the proximal direction, are connected to each other so that this on its own produces a certain stabilising effect. The stabilising effect is reinforced by the fact that the interconnected third sections of the loop-shaped ends 25a, 25b brought back in the proximal direction are connected to non-branched first braid ends 13b so that the loop-shaped ends 25a, 25b are fixed on two sides, ie both in the region of the first section 26a extending in the distal direction and in the region of the third section 26c brought back in the proximal direction.

In addition to the embodiment according to FIG. 26, it is provided with the exemplary embodiment according to FIG. 28 that further loop-shaped ends 25c, 25d are provided overlapping a plurality of first braid ends 13a, 13b. The formation of the additional loop-shaped ends 25c, 25d is performed similarly to form the above-described loop-shaped ends 25a, 25b, namely by branching or dividing a first braid end 13a on the one hand and by connection of the third section of the respective additional loop-shaped end 25c, 25d brought back in the proximal direction with another proximal third section and a non-branched first braid end 13b. To this end, the multiple-branching first braid ends 13c comprise a larger number of wire ends 12, for example, eight wire ends 12. The eight wire ends are divided into four groups with two wire ends 12 each, wherein two groups form the next two loop-shaped ends 25a, 25b (non-branched), which connect the two braid ends 13b in opposed circumferential directions. The two other loop-shaped ends 25d, 25c comprise in each case two wire ends 12, which bridge a plurality of first braid ends 13a, 13b and are brought together in the region of a multiple connection point. This means that a plurality of first braid ends 13a, 13b are distributed on the circumference which are formed from eight wire ends 12, wherein in each case two braid ends formed from four wire ends 12 are arranged between the braid ends formed from eight wire ends 12. A different number of wire ends for each multiple-branching braid end, for example 10, 12, 14 or more than 14, is possible. The number of braid ends 13a, 13b arranged between the multiple-branching or multiple-connecting braid ends 13a, 13b comprise a smaller number of wire ends 12, particularly half the number of the wire ends 12 of multiple-branching or multiple-connecting braid ends 13a, 13b.

The number of the overlapping first braid ends 13a, 13b can be varied as required. It is also possible to provide more than the two planes shown in FIG. 28, wherein the principle shown in FIG. 28 is extended or continued accordingly.

Figure 29:
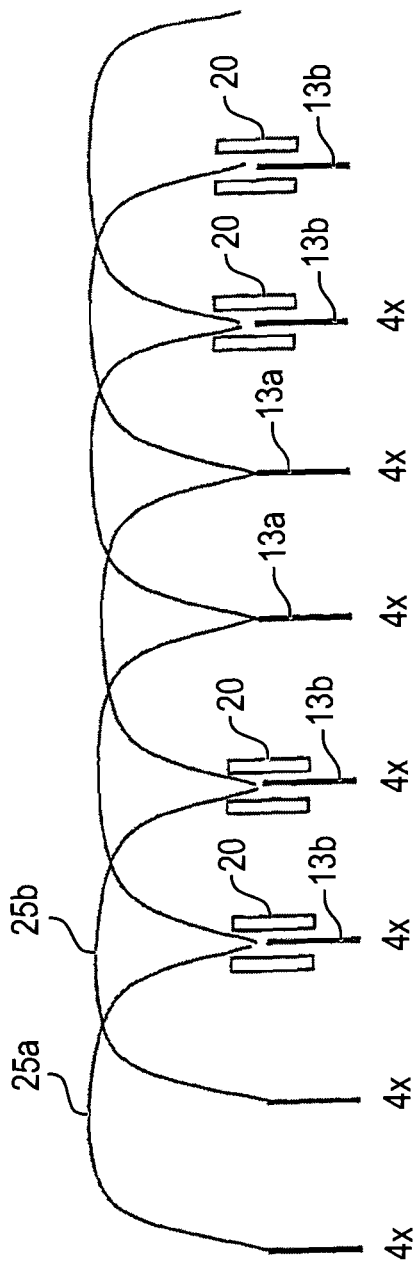

With the exemplary embodiment according to FIG. 29, the loop-shaped ends 25a, 25b are arranged so that they overlap. This is achieved in that the loop-shaped ends 25a or 25b in each case overlap a first braid end 13b so that a loop-shaped end 25a connects every second braid end 13b. Hereby, in each case two branching first braid ends 13a are arranged in the circumferential direction adjacent and next to each other. The same applies to the connecting first braid ends 13b, which are also arranged in each case in pairs or generally grouped in each case.

Here, once again it is possible to vary the number of wire ends 12 for each braid end 13a, 13b.

With above-described exemplary embodiments, the second circumferential section 16b is formed by the loop-shaped ends 25a, 25b, which correspond to the second braid ends 14a, 14b. The first circumferential section 16a is formed by the first braid ends 13a, 13b, which fix loop-shaped ends 25a, 25b in such a way that the loop-shaped ends 25a, 25b are connected to each other at least in the transitional region between the first and second circumferential section 16a, 16b. With the exemplary embodiments according to FIGS. 26 to 30, the second circumferential section 16b forms an atraumatic end section abutting the axial end of the implant or the stent. The connecting region or the punctiform connecting region between the loop-shaped ends 25a, 25b and the first braid ends 13a, 13b can be seen as a transitional region between the first and second circumferential section.

As shown in FIG. 26, the second circumferential section 16b insofar follows the first circumferential section 16a in sequence in the longitudinal direction in that at least the curved second section 26b of the loop-shaped ends 25a, 25b is arranged downstream of first braid ends 13a extending in the axial direction.

Figures 30A, 30B:
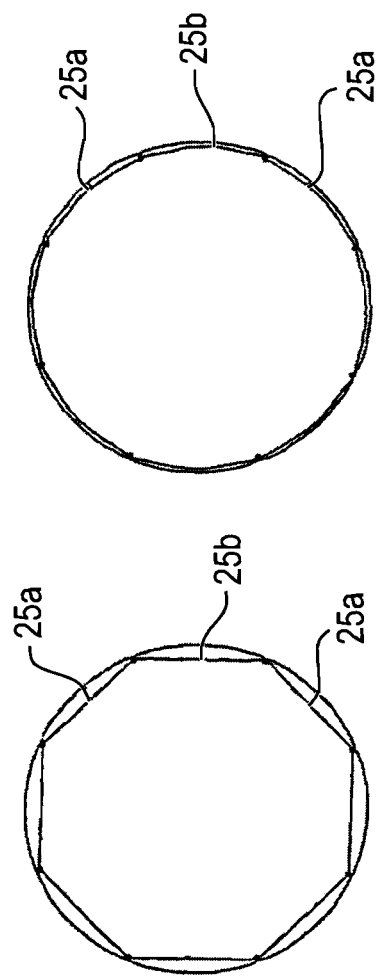

FIGS. 30a, 30b show the behaviour of the loop-stabilised stent ends in the vessel. The advantage of the loop-shaped ends 25a, 25b consists in the fact that they have a cylindrical profile so that they lie on the vascular wall without protruding into the lumen.

In production, the connection of the braid ends, which are marked in FIG. 30a by dots, results in loops. The deformation of the loops in production causes these loops to adopt a cylindrical profile, as shown in FIG. 30b. In production, the loop-shaped ends 25a, 25b are deformed in such a way that they adopt the radius of the stent or the target vessel. This can for example take place in that the wires are produced from a shape-memory material, for example nitinol, wherein the loop-shaped ends 25a, 25b are held on a mandrel and then treated with heat so the corresponding conditioning takes place.

The function or effect of the mutually stabilising loops or loop-shaped ends 25a, 25b is achieved by the equilibrium of forces in the region of the stent end. The equilibrium of forces results from the symmetry of the arrangement, in which the individual loop-shaped ends 25a, 25b are connected to each other and in this way have a mutually fixing effect.

Figure 31A:
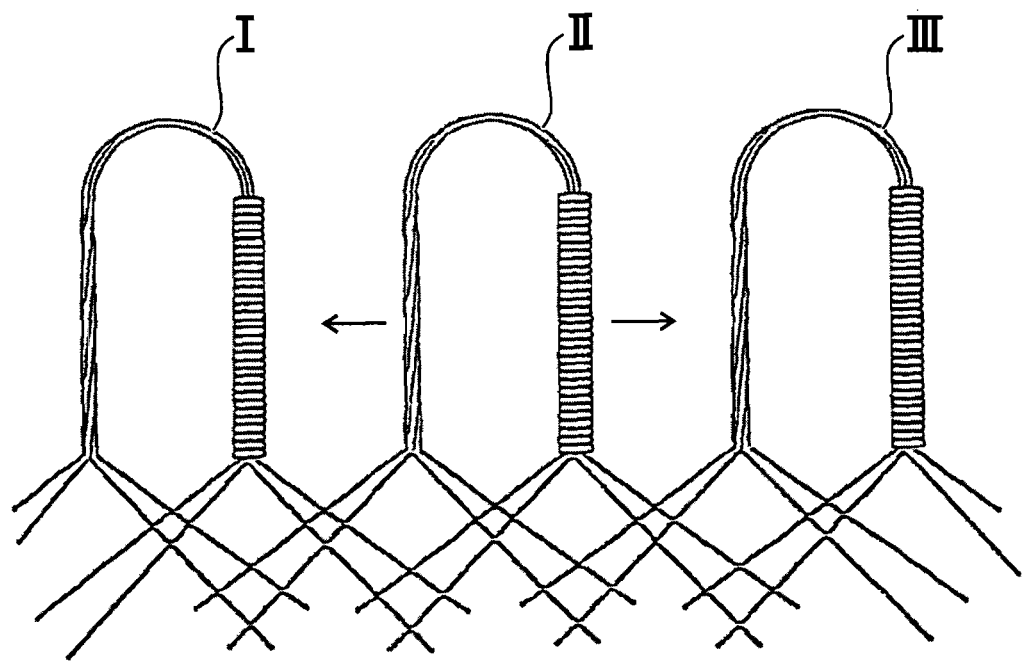
Figure 31B:
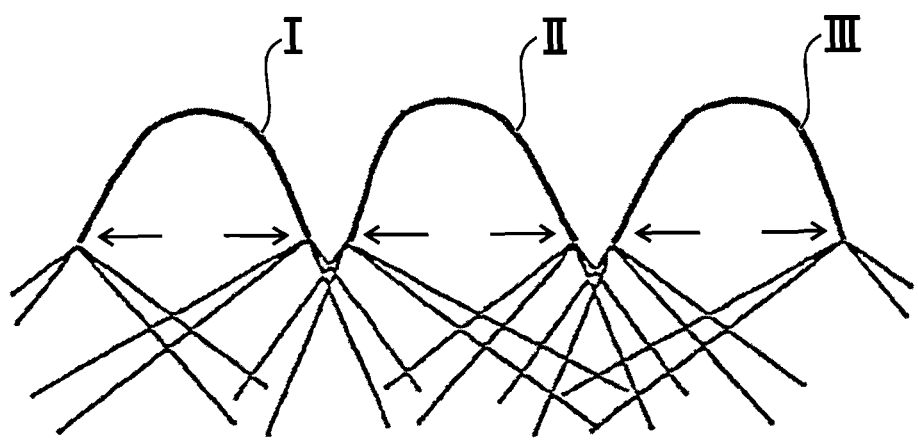
Figure 31C:
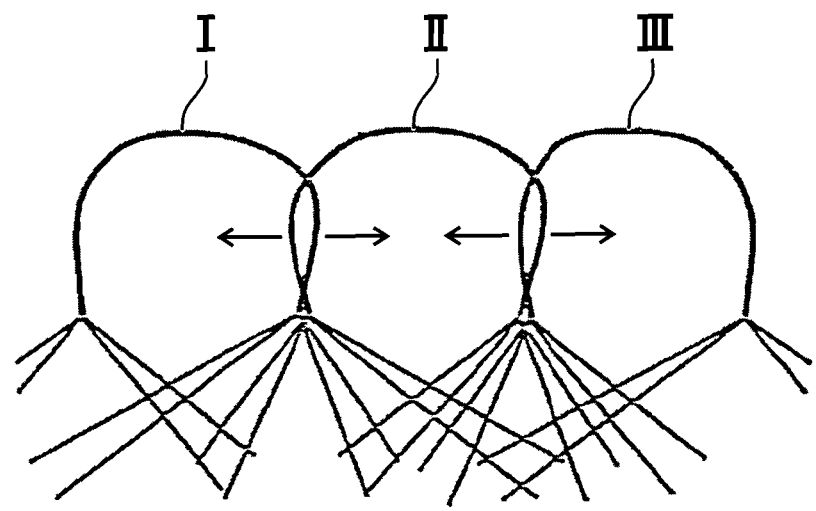

Contrary to this, with non-stabilised loop configurations, such as, for example, shown in FIGS. 31a to 31d, the restoring force of the individual loop results in a relative movement of the respective braid ends, wherein the respective braid ends are pressed apart. The result is that two ends of adjacent loops approach each other (FIG. 31b). The force of the loops, resulting in the displacement of the ends, does not contribute to the expansion of the diameter of the stent. Contrary to this, with the exemplary embodiments according to FIGS. 26 to 30, all braid ends move apart from each other which results in the expansion of the stent diameter, including in the region of the axial ends.

Figure 31D:
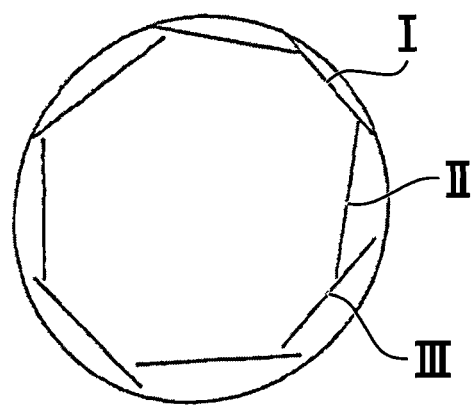

The principle on which the exemplary embodiments according to FIGS. 26 to 30 are based prevents any overlapping of the loops, because, with the exemplary embodiments according to FIGS. 26 to 30, two adjacent loops share a common end. In this context, overlapping is not desired (FIG. 31c) and does not correspond to the deliberately established overlapping of the loop-shaped ends 25a, 25b according to FIG. 29. The loop-stabilised braid ends prevent the loops in the vascular lumen from protruding inward, as is the case with a non-stabilised configuration (FIG. 31d).

List of Reference Numbers
10a, 10b, 10c, 10d Wires
11 Wall
12a, 12b Wire ends 13a, 13b First braid ends
14a, 14b Second braid ends
15a, 15b Further braid ends
16a First circumferential section
16b Second circumferential section
16c Further circumferential sections
17a, 17b Connecting sections
18a, 18b End faces
19a Curved region
19b Connecting region
20 Connecting element
21 Middle section
22 Connecting ends
23 Multiple connector
24 Crossover points
25a, 25b, 25c, 25d Loop-shaped ends
26a, 26b, 26c 1st, 2nd, 3rd section
27a, 27b Groups

The invention claimed is:

1. A medical implant, comprising:
a stent wall including a circumferential section,
wherein the circumferential section includes:
a first section formed by wires, the first section extending along a longitudinal axis of the stent wall, and
a second section formed by a braid formed by braiding the wires, the second section extending along the longitudinal axis and curving around the longitudinal axis,
wherein ends of the wires of the first section are connected to an end of the braid of the second section.

2. The medical implant according to claim 1, further comprising:
an axial end, the axial end including a plurality of loop-shaped sections disposed adjacent with each other and connected to each other along a circumferential direction,
wherein each of the loop-shaped sections includes:
a first portion extending in a distal direction,
a curved second portion, and
a third portion extending in a proximal direction, wherein the curved second portion is connected to and disposed between the first portion and the third portion, and
at least one of the loop-shaped sections is connected to the second section of the stent wall.

3. The medical implant according to claim 2, wherein each of the loop-shaped sections includes the braid connected to the wires.

4. The medical implant according to claim 3, wherein the loop-shaped sections are arranged in parallel with each other.

5. The medical implant according to claim 2, wherein the loop-shaped sections are connected to each other mechanically or adhesively.

6. The medical implant according to claim 2, wherein the loop-shaped sections define a plurality of overlapping planes.

7. The medical implant according to claim 2, wherein the loop-shaped sections are arranged overlappingly.

8. The medical implant according to claim 1, wherein the stent wall comprises more than two of the circumferential sections arranged in sequence along the longitudinal direction and connected together.

9. The medical implant according to claim 8, wherein each of the circumferential sections includes a connecting section, wherein the connecting section of one of the circumferential sections is arranged in an opposite direction and connected to the connecting section of another one of the circumferential sections.

10. The medical implant according to claim 9, wherein the connected connecting sections are arranged with their end faces in a face-to-face arrangement, or the connecting sections are arranged to form an angle α.

11. The medical implant according to claim 1, wherein the braid includes a connecting section, wherein the connecting section is arranged in the same direction as another connecting section of another braid, and the connecting section and the another connecting section are connected to each other.

12. The medical implant according to claim 1, wherein the ends of the wires of the first section connected to the end of the braid of the second section have the same angle of twist as the end of the braid.

13. The medical implant according to claim 1, wherein at least one of the ends of the wires of the first section connected to the end of the braid of the second section has an angle of twist that is different from an angle of twist at the end of the braid.

14. The medical implant according to claim 1, wherein the second section includes a curved region between the end of the braid and another end of the braid.

15. The medical implant according to claim 1, wherein the braid is formed by the wires that are twisted.

16. The medical implant according to claim 1, wherein 3 or more of the wires form the braid.

17. The medical implant according to claim 15, wherein an angle of twist of at least one of the wires forming the braid is greater than 10°.

18. The medical implant according to claim 1, wherein the second section includes a connecting element disposed between the end of the braid and another end of the braid.

19. The medical implant according to claim 18, wherein the connecting element is elastic.

20. The medical implant according to claim 18, wherein the connecting element can be changed from an expanded state to a compressed state.

21. The medical implant according to claim 20, wherein, in the expanded state, the connecting element applies a force to push apart the end of the braid from the another end of the braid.

22. The medical implant according to claim 18, wherein the connecting element comprises a connecting coil, a connecting sleeve, or connecting wires.

23. The medical implant according to claim 18, wherein the connecting element comprises a middle section with connecting ends, wherein the connecting ends are respectively connected to the end of the braid and the another end of the braid.

24. The medical implant according to claim 23, wherein the middle section is U-shaped.

25. The medical implant according to claim 18, wherein the connecting element comprises a multiple connector for connecting more than two braid ends.

26. A medical implant, comprising:
a stent wall including a braid of wires extending along a longitudinal axis and curving around the longitudinal axis,
wherein at least two wire ends of the wires are connected to a braid end, and arranged on a first circumferential section of the stent wall extending around the longitudinal axis,
wherein the wires, having the at least two wire ends connected to the braid end have the same direction of twist, and
the braid end is arranged along a circumferential direction of the stent wall.

27. A method for producing a medical implant, comprising:

braiding wires to form a braid for a stent wall of the medical implant, the braid including two braid ends, wherein each of the two braid ends is connected to ends of the wires.

28. A method for producing a medical implant, comprising:
- forming a stent wall of the medical implant by forming a braid,
- wherein the forming the braid includes connecting wires so that ends of the wires are connected to each other to form an end of the braid, and twisting the wires to have the same direction of twist, and
- arranging the braid along a circumferential direction of the stent wall.

* * * * *